(12) United States Patent  
Beard et al.

(10) Patent No.: US 8,097,644 B2
(45) Date of Patent: Jan. 17, 2012

(54) INDOLE COMPOUNDS HAVING SPHINGOSINE-1-PHOSPHATE (S1P) RECEPTOR ANTAGONIST

(75) Inventors: Richard L. Beard, Newport Beach, CA (US); John E. Donello, Dana Point, CA (US); Haiqing Yuan, Irvine, CA (US); Vidyasagar Vuligonda, Irvine, CA (US); Tien T. Duong, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/690,637

(22) Filed: Mar. 23, 2007

(65) Prior Publication Data

US 2007/0232682 A1    Oct. 4, 2007

Related U.S. Application Data

(60) Provisional application No. 60/786,683, filed on Mar. 28, 2006.

(51) Int. Cl.
*A61K 31/405*  (2006.01)
*C07D 209/04* (2006.01)

(52) U.S. Cl. .......................................... 514/415; 548/510
(58) Field of Classification Search .................... None
See application file for complete search history.

(56) References Cited

U.S. PATENT DOCUMENTS

| | | | |
|---|---|---|---|
| 4,952,683 A | 8/1990 | Tschannen et al. | |
| 5,102,901 A | 4/1992 | vanWijngaarden et al. | |
| 5,110,987 A | 5/1992 | Liotta et al. | |
| 5,294,722 A | 3/1994 | Kim | |
| 5,403,851 A | 4/1995 | D'Orlando et al. | |
| 5,580,878 A | 12/1996 | D'Orlando et al. | |
| 6,235,912 B1 | 5/2001 | Takesako et al. | |
| 6,239,297 B1 | 5/2001 | Takesako et al. | |
| 6,358,992 B1 * | 3/2002 | Pamukcu et al. | 514/414 |
| 2003/0125371 A1 | 7/2003 | Elokdah et al. | |
| 2007/0191313 A1 | 8/2007 | Liu et al. | |
| 2007/0232682 A1 | 10/2007 | Beard et al. | |

FOREIGN PATENT DOCUMENTS

| | | |
|---|---|---|
| WO | WO03-062252 | 7/2003 |
| WO | WO2004-096752 | 7/2004 |
| WO | WO2004-071442 | 8/2004 |
| WO | WO2004-103306 | 12/2004 |
| WO | WO2007-064841 | 3/2007 |
| WO | WO2008-050695 | 1/2008 |

OTHER PUBLICATIONS (Acute Respiratory Distress Syndrome) http://en.wikipedia.org/wiki/Acute_respiratory_distress_syndrome (2007).*
Bartolini et al, caplus an 2007:672966.*
Mukhanova et al, caplus an 1994:700708.*
Muhkanova et al., caplus an 1994:700708.*
Clemens et al, Bioorg. Med. Chem. Lett. 13, 3401-3404, 2003.
Hale et al, Bioorg. Med. Chem. Lett. 14, 3351-3355, 2004.
Hale et al, Bioorg. Med. Chem. Lett. 14, 3495-3499, 2004.
Yan et al, Bioorg. Med. Chem. Lett. 14, 4861-4866, 2004.
Clemens et al, Bioorg. Med. Chem. Lett. 14, 4903-4906, 2004.
Hale et al, Bioorg. Med. Chem. Lett. 14, 3501-3505, 2004.
Hale et al, J.. Med. Chem., 47, 6662-6665, 2004.
U.S. Appl. No. 60/884,470, filed Jan. 11, 2007, Richard L. Beard.
U.S. Appl. No. 60/786,683, filed Mar. 28, 2006, Richard L. Beard.

* cited by examiner

*Primary Examiner* — Sun Jae Loewe
(74) *Attorney, Agent, or Firm* — Doina G. Ene; John E. Wurst; Kevin J. Forrestal

(57) ABSTRACT

The present invention provides novel compounds having the following general formula I

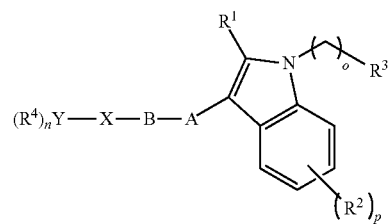

wherein: A, B, X, Y, $R^1$, $R^2$, $R^3$, $R^4$, n, o and p are as defined in the specification. Such compounds are useful for treating a disease or condition selected from the group consisting of glaucoma, dry eye, angiogenesis, cardiovascular conditions or diseases and wound healing.

7 Claims, No Drawings

INDOLE COMPOUNDS HAVING SPHINGOSINE-1-PHOSPHATE (S1P) RECEPTOR ANTAGONIST

CROSS REFERENCE TO RELATED APPLICATIONS

This application claims priority to U.S. Provisional Application No. 60/786,683, filed Mar. 28, 2006, which is expressly incorporated herein by reference in its entirety.

BACKGROUND OF THE INVENTION

1. Field of the Invention

The present invention relates to derivatives and/or analogues of sphingosine and pharmaceutical compositions, including such derivatives and/or analogues, which are useful as drugs for the treatment of fungal infections, allergic diseases, immune disorders, etc.

2. Summary of the Art

Sphingosine is a compound having the chemical structure shown in the general formula described below, in which $Y^1$ is hydrogen. It is known that various sphingolipids, having sphingosine as a constituent, are widely distributed in the living body including on the surface of cell membranes of cells in the nervous system.

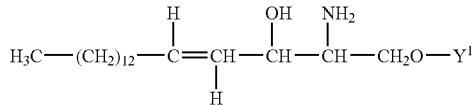

A sphingolipid is one of the lipids having important roles in the living body. A disease called lipidosis is caused by accumulation of a specified sphingolipid in the body. Sphingolipids present on cell membranes function to regulate cell growth; participate in the development and differentiation of cells; function in nerves; are involved in the infection and malignancy of cells; etc. Many of the physiological roles of sphingolipids remain to be solved. Recently the possibility that ceramide, a derivative of sphingosine, has an important role in the mechanism of cell signal transduction has been indicated, and studies about its effect on apoptosis and cell cycle have been reported.

Sphingosine-1-phosphate is an important cellular metabolite, derived from ceramide that is synthesized de novo or as part of the sphingomeyeline cycle (in animals cells). It has also been found in insects, yeasts and plants.

The enzyme, ceramidase, acts upon ceramides to release sphingosine, which is phosphorylated by spingosine kinase, a ubiquitous enzyme in the cytosol and endoplasmic reticulum, to form sphingosine-1-phosphate. The reverse reaction can occur also by the action of sphingosine phosphatases, and the enzymes act in concert to control the cellular concentrations of the metabolite, which concentrations are always low. In plasma, such concentration can reach 0.2 to 0.9 µM, and the metabolite is found in association with the lipoproteins, especially the HDL. It should also be noted that sphingosine-1-phosphate formation is an essential step in the catabolism of sphingoid bases.

Like its precursors, sphingosine-1-phosphate is a potent messenger molecule that perhaps uniquely operates both intra- and inter-cellularly, but with very different functions from ceramides and sphingosine. The balance between these various sphingolipid metabolites may be important for health.

For example, within the cell, sphingosine-1-phosphate promotes cellular division (mitosis) as opposed to cell death (apoptosis), which it inhibits. Intracellularly, it also functions to regulate calcium mobilization and cell growth in response to a variety of extracellular stimuli. Current opinion appears to suggest that the balance between sphingosine-1-phosphate and ceramide and/or spingosine levels in cells is critical for their viability. In common with the lysophospholipids, especially lysophosphatidic acid, with which it has some structural similarities, sphingosine-1-phosphate exerts many of its extra-cellular effects through interaction with five specific G protein-coupled receptors on cell surfaces. These are important for the growth of new blood vessels, vascular maturation, cardiac development and immunity, and for directed cell movement.

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular disease. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

Fungi and plants have sphingolipids and the major sphingosine contained in these organisms has the formula described below. It is known that these lipids have important roles in the cell growth of fungi and plants, but details of the roles remain to be solved.

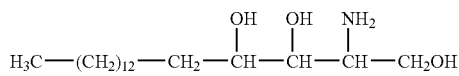

Recently it has been known that derivatives of sphingolipids and their related compounds exhibit a variety of biological activities through inhibition or stimulation of the metabolism pathways. These compounds include inhibitors of protein kinase C, inducers of apoptosis, immuno-suppressive compounds, antifungal compounds, and the like. Substances having these biological activities are expected to be useful compounds for various diseases.

Derivatives of sphingosine have been prepared in various patents. For example, see U.S. Pat. Nos. 4,952,683, 5,110,987, 6,235,912 B1, 6,239,297 B1.

Also, compounds which are similar to certain spingosine derivatives, but which are not reported as being ligands for the spingosine receptors are reported in various patents. See for example, U.S. Pat. Nos. 5,294,722, 5,102,901, 5,403,851, 5,580,878. U.S. Patent Application Publication No. US 2003/0125371 A2. While certain of the compounds reported in the above patents are indoles, it does not appear that indole compounds have been reported as being ligands for sphingosine receptor or having activity as sphingosine agonists or antagonists.

SUMMARY OF THE INVENTION

The present invention provides a derivative or analogue of sphingosine that is able to regulate the functions of sphingolipid, and pharmaceutical compositions comprising said derivative or analogue.

These compounds are represented by the formula I, each of which compounds may have sphingosine-1-phosphate receptor agonist and or antagonist biological activity

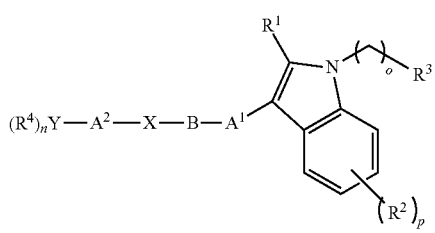

wherein:

$A^1$ and $A^2$ are independently selected from the group consisting of $(CH_2)m$ where m is 0 or an integer of from 1 to 6, lower branched chain alkyl having 2 to 6 carbons, cycloalkyl having 3 to 6 carbons, alkenyl having 2 to 6 carbons and 1 or 2 double bonds, alkynyl having 2 to 6 carbons and having 1 or 2 triple bonds, $NR^5$, O and S;

B is selected from the group consisting of $(CH_2)n$, where n is 0 or an integer of from 1 to 6, lower branched chain alkyl having 2 to 6 carbons, cycloalkyl having 3 to 6 carbons, alkenyl having 2 to 6 carbons and 1 or 2 double bonds, alkynyl having 2 to 6 carbons and having 1 or 2 triple bonds, C=C $(R^5)_2$, C=O, C=S, $R^5C$=$NR^5$, $R^5C$=$CR^5$, C=$NOR^5$, $CR^5OR^5$, $C(OR^5)_2$, $CR^5N(R^5)_2$, $C(N(R^5)_2)_2$, $CR^5SR^5$, $C(SR^5)_2$, SO, $SO_2$, and heterocyclic aryl comprising from 2 to 14 carbon atoms and from 1 to 3 heteroatoms selected from the group consisting of nitrogen, oxygen and sulfur;

X is selected from the group consisting of $(CH_2)r$, where r is 0 or an integer of from 1 to 6, lower branched chain alkyl having 2 to 6 carbons, cycloalkyl having 3 to 6 carbons, alkenyl having 2 to 6 carbons and 1 or 2 double bonds, alkynyl having 2 to 6 carbons and having 1 or 2 triple bonds, $NR^5$, O and S;

provided that when m is 0 and B is C=O then X is not $NR^5$, O or S;

Y is $R^6$, or a carbocyclic aryl group comprising from 6 to 14 carbon atoms or a heterocyclic aryl group comprising from 2 to 14 carbon atoms and from 1 to 3 heteroatoms selected from the group consisting of nitrogen, oxygen and sulfur, and, preferably, Y is a phenyl group, or heterocyclic aryl group selected from the group consisting of pyridyl, thienyl, furyl, pyradizinyl, pyrimidinyl, pyrazinyl, thiazolyl, oxazolyl, and imidazolyl;

o is 0 or an integer of from 1 to 3;

p is 0 or an integer of from 1 to 4;

$R^1$, $R^2$, $R^3$, $R^4$ are independently selected from the group consisting of hydrogen, straight or branched chain alkyl having 1 to 12 carbons, cycloalkyl having 3 to 6 carbons, alkenyl having 2 to 6 carbons and 1 or 2 double bonds, alkynyl having 2 to 6 carbons and 1 or 2 triple bonds, aryl, preferably a carbocyclic aryl group having from 6 to 14 carbon atoms or a heterocyclic aryl group having from 2 to 14 carbon atoms and from 1 to 3 heteroatoms selected from the group consisting of nitrogen, oxygen and sulfur, halo, e.g. fluoro or chloro, $C_1$ to $C_{12}$ haloalkyl, e.g. trifluoromethyl, hydroxyl, $C_1$ to $C_{12}$ alkoxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl, sulfonyl,

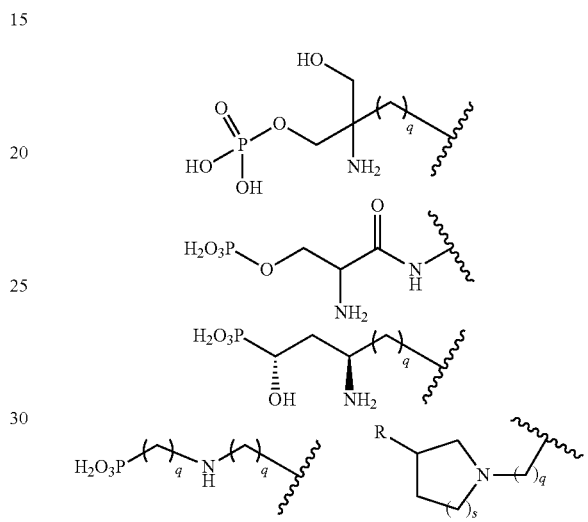

wherein R is $CO_2H$ or $PO_3H_2$ and q is 0 or an integer of 1 to 5 and s is 0 or an integer from 1 to 3;

$R^5$ is selected from the group consisting of hydrogen, straight or branched chain alkyl having 1 to 12 carbons, cycloalkyl having 3 to 6 carbons, alkenyl having 2 to 6 carbons and 1 or 2 double bonds, alkynyl having 2 to 6 carbons and 1 or 2 triple bonds, aryl, preferably a carbocyclic aryl group having from 6 to 14 carbon atoms or a heterocyclic aryl group having from 2 to 14 carbon atoms and from 1 to 3 heteroatoms selected from the group consisting of nitrogen, oxygen and sulfur, halo, e.g. fluoro or chloro, $C_1$ to $C_{12}$ haloalkyl, hydroxyl, $C_1$ to $C_{12}$ alkoxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl, and sulfonyl; and $R^6$ is selected from the group consisting of straight or branched chain alkyl, having 1 to 12 carbons, cycloalkyl having 3 to 6 carbons, alkenyl having 2 to 6 carbons and 1 or 2 double bonds and alkynyl having 2 to 6 carbons and 1 or 2 triple bonds.

The aryl group is any carbocyclic aryl or heterocyclic aryl group including but not limited to benzene, pyridine, pyrazine, pyridazine, pyrimidine, triazine, thiophene, furan, thiazole, thiadiazole, isothiazole, oxazole, oxadiazole, isooxazole, naphthalene, quinoline, tetralin, chroman, thiochroman, tetrahydroquinoline, dihydronaphthalene, tetrahydronaphthalen, chromene, thiochromene, dihydroquinoline, indan, dihydrobenzofuran, dihydrobenzothiophene, indene, benzofuran, benzothiophene, coumarin and coumarinone. Such aryl groups can be bonded to the above moiety at any position. Such aryl group may itself be substituted with any common organic functional group including but not limited to alkyl, alkenyl, alkynyl, aryl, halo, haloalkyl, hydroxyl, alkoxyl, alkylcarbonyl, formyl, oxycarbonyl, carboxyl, alkyl carboxylate, alkyl amide, aminocarbonyl, amino, cyano, diazo, nitro, thio, sulfoxyl, or sulfonyl groups.

Preferably, the carbocyclic aryl group will comprise from 6 to 14 carbon atoms, e.g. from 6 to 10 carbon atoms. Preferably the heterocyclic aryl group will comprise from 2 to 14 carbon atoms and one or more, e.g. from 1 to 3 heteroatoms selected from the group consisting of nitrogen, oxygen and sulfur.

Preferably, $R^1$ is i-propyl.
Preferably, $R^2$ is OH.
Preferably, $R^3$ is benzyl.
Preferably, $R^4$ is selected from the group consisting of propyl and phenyl, e.g. 2,4 difluorophenyl
Preferably, B is C=O.
Preferably, $A^1$ and $A^2$ are absent.
Preferably, X is selected from the group consisting of $C_2H_2$, $CH_2$ and $C_2H_2$.

Specific Examples of the compounds of formula I include

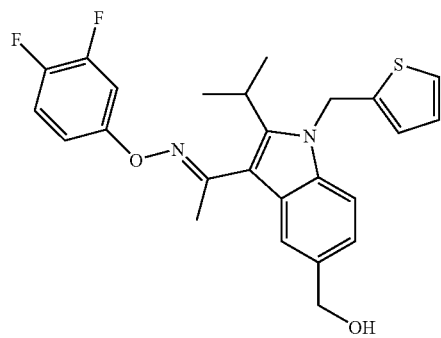

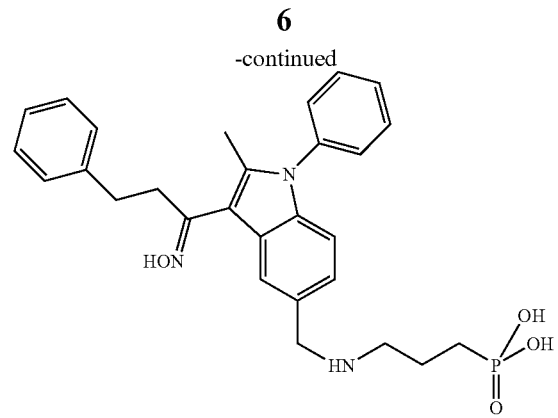

-continued

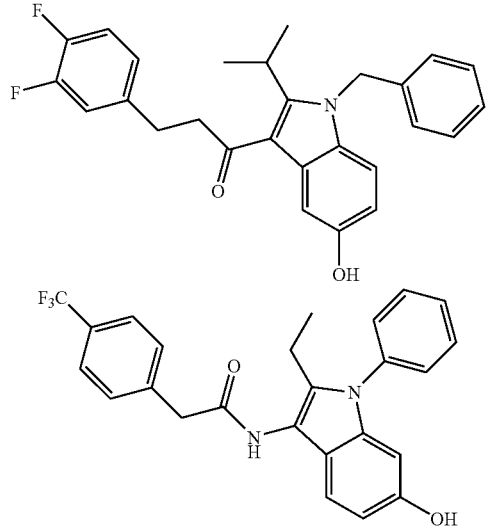

These compounds may be synthesized as illustrated by the synthesic schemes depicted below:

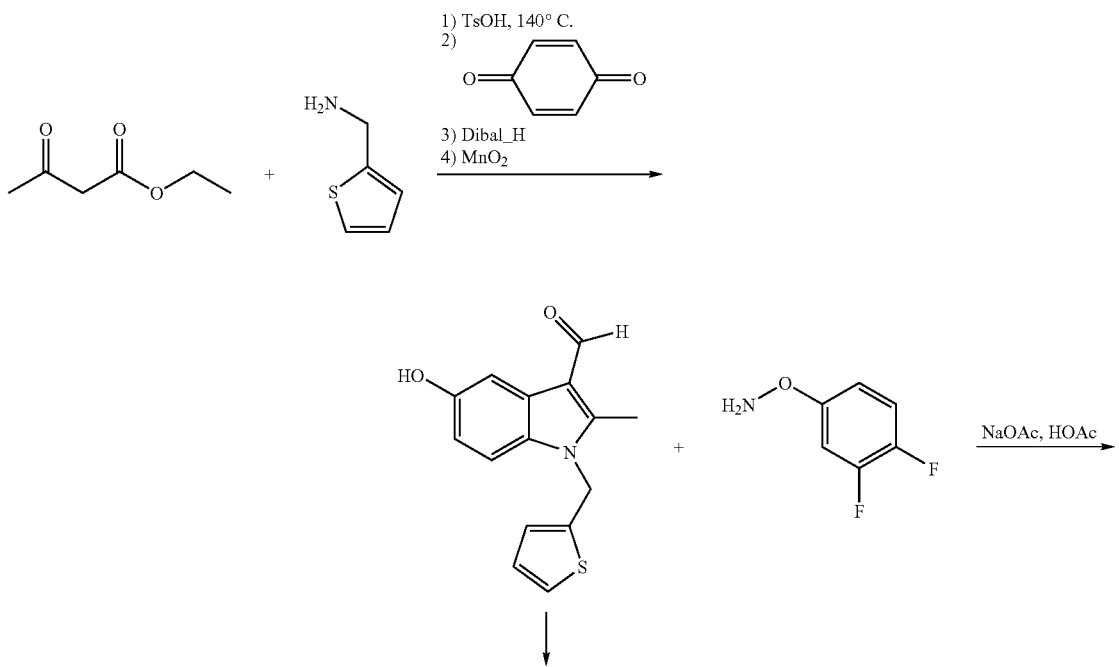

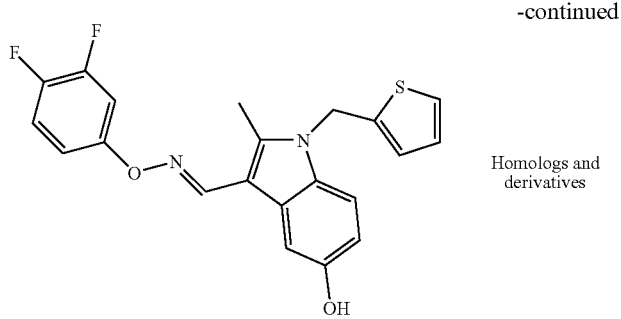
Homologs and derivatives

Compounds with oxime linking groups in the 3 position of the indole ring system can be prepared generally as depicted in Scheme 1. A beta-ketoester (e.g. ethyl acetoacetate) is treated with an amine (e.g. 2-thiophenemethyl amine) in the presence of an organic acid (e.g. para-toluenesulfonic acid) and 1,4-benzoquinone to produce a 5-hydroxyindole-3-carboxylic acid ester (e.g. 5-hydroxy-2-methyl-1-(2-thiophenemethyl)indole-3-carboxylic acid, ethyl ester). The carboxylic acid ester group can be reduced to a primary alcohol with various reducing agents such as diisobutylaluminum hydride (Dibal) and then oxidized to an aldehyde with a mild oxidizing agent such as manganese dioxide to produce a 5-hydroxyindole-3-carboxaldehyde (e.g. 5-hydroxy-2-methyl-1-(2-thiophenemethyl)indole-3-carbaldehyde). Treatment of this aldehyde with an alkyl or aryl oxime (e.g. O-(3,4-difluorophenyl)oxime) in a buffer solution (sodium acetate and acetic acid in methanol and water) will result in the formation of a 3-oxime-linked compound (e.g. 5-hydroxy-2-methyl-1-(2-thiophenemethyl)indole-3-carbaldehyde, O-(3,4-difluorophenyl)oxime). Moreover, this aldehyde, or a similar compound, will be recognized by those skilled in the art as a versatile intermediate which may be converted into a number of homologs and derivatives which are included within the scope of this invention.

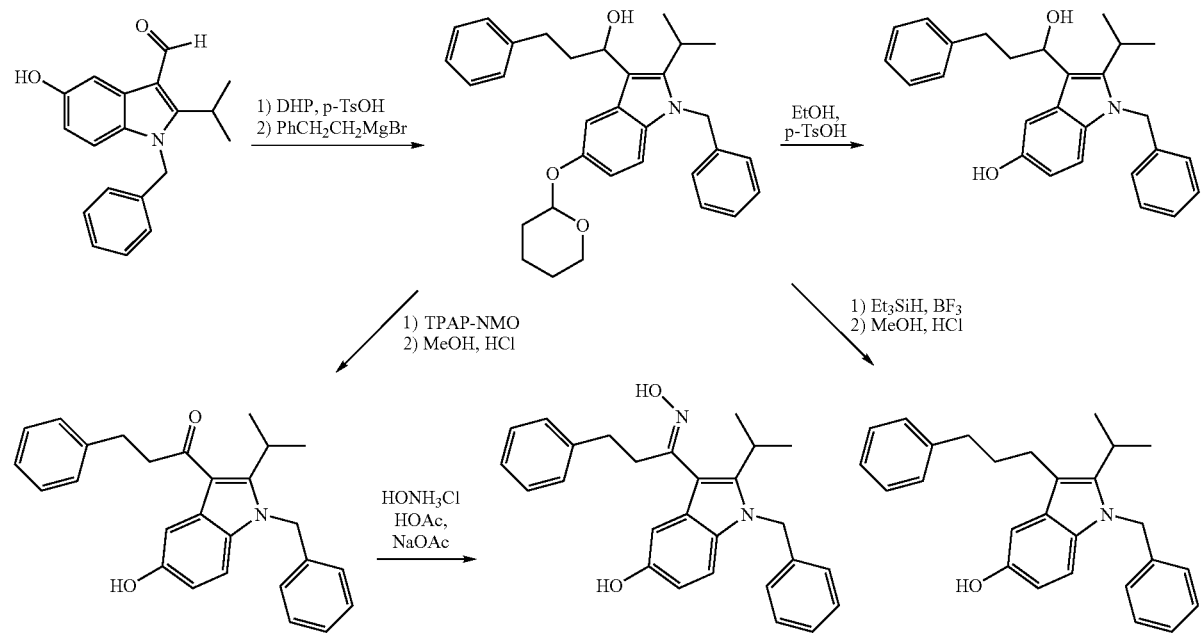

SCHEME 2

Compounds with various linking groups in the 3 position of the indole ring system can be prepared generally as depicted in Scheme 2. After protection of the 5-hydroxyindole group with dihydropyran in the presence of an acid catalyst (p-toluenesulfonic acid, p-TsOH), the 3-aldehyde group can be reacted with an alkyl or aryl Grignard Reagent (e.g. benzylmagnesium bromide) in an inert solvent (THF) to produce a secondary alcohol. This compound can be treated directly with alcohol in the presence of p-TsOH to remove the tetrahydropyran (THP) protecing group to produce an alcohol-linked indole (e.g. 1-(1-benzyl-5-hydroxy-2-isopropyl-1H-indol-3-yl)-3-phenylpropan-1-ol). Alternatively, the secondary alcohol may be oxidized with various oxidizing agents such as tetrapropylammonium perruthenate (TPAP) and N-methylmorpholine, N-oxide (NMO) to produce ketone-linked products (e.g. 1-(1-benzyl-5-hydroxy-2-isopropyl-1H-indol-3-yl)-3-phenylpropan-1-one), or the secondary alcohol may be reduced with various reducing agents such as triethlylsilane (Et₃SiH) and boron trifluoride (BF₃) to produce alkyl-linked products (e.g. 1-(1-benzyl-5-hydroxy-2-isopropyl-1H-indol-3-yl)-3-phenylpropane). Those skilled in the art will recognize that the ketone-linked products can be reacted further to produce other homologs and derivatives within the scope of the invention, such as oxime derivatives (eg. 1-(1-benzyl-5-hydroxy-2-isopropyl-1H-indol-3-yl)-3-phenylpropan-1-one oxime).

SCHEME 3

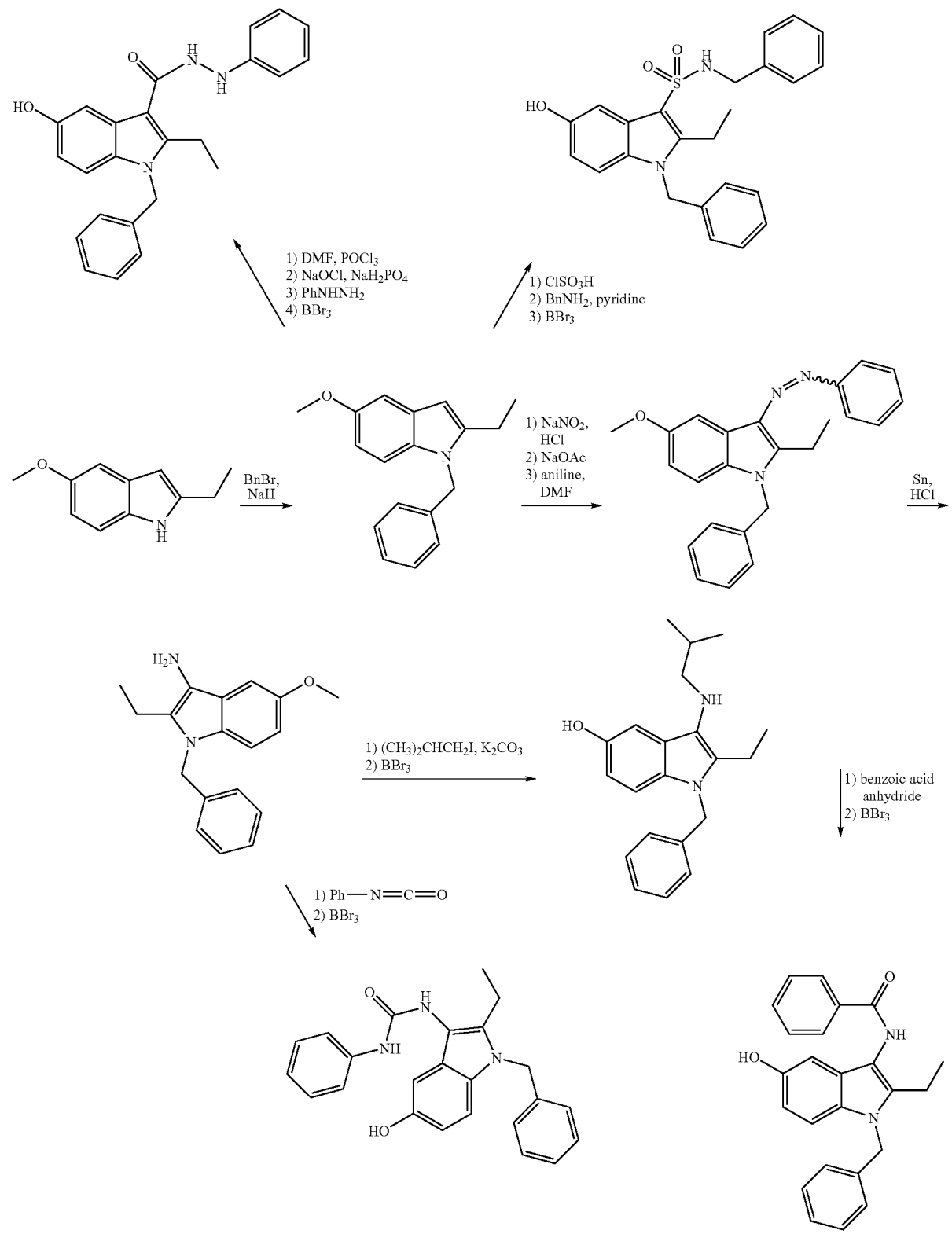

Compounds with nitrogen-linked groups in the 3 position of the indole ring system can be prepared generally as depicted in Scheme 3. Thus, a substituted indole can be N-alkylated by treatment with an alkyl bromide (e.g. benzyl bromide) in the presence of a strong base such as sodium hydride to produce an N-alkylated indole, which is a versatile intermediate that can be used to make several compounds within the scope of the invention. For instance, the N-alkylated indole may be reacted with nitrous acid and an aromatic amine (e.g. aniline) to give an azo compound (e.g. N-(1-benzyl-2-ethyl-5-methoxy-1H-indol-3-yl)-N-phenylhydrazine). Amides (e.g. benzoic acid, 1-benzyl-2-ethyl-5-methoxy-1H-indol-3-carbamide) can be produced directly from the azo compound by reacting it with alkyl or aryl carboxylic acid anhydrides. Alternatively, the azo compound can be treated with tin and hydrochloric acid to produce a 3-aminoindole, which is a versatile intermediate that can be converted to several homologs and derivatives, including alkyl and aryl amines, amides, carbamates, ureas and thioureas. For example, treating the 3-amino indole with an alkyl iodide in the presence of base will produce a 3-N-alkylaminoindole (e.g. N-(1-benzyl-2-ethyl-5-methoxy-1H-indol-3-yl)-N-(2-methylpropyl)amine). As a second example, the 3-aminoindole can be reacted with alkyl or aryl isocyanates to produce urea-linked indoles (e.g. N-(1-benzyl-2-ethyl-5-methoxy-1H-indol-3-yl)-N'-phenylurea). Alternatively, the N-alkylated indole may be reacted with chlorosulfonic acid and an amine in the resence of pyridine to produce 3-alkylsulfonamide derivatives (e.g. N-benzyl-3-benzylsulfonamido-2-ethyl-5-hydroxyindole). In addition, the N-alkylated indole can undergo a carboxylation reaction (DMF, POCl3, then NaOCl and NaH2PO4) to produce the 3-carboxyindole, which can be reacted further to produce compounds within the scope of the invention, such as N-benzyl-3-phenylhydrazido-2-ethyl-5-hydroxyindole. Other examples are reported in the experimental section.

DETAILED DESCRIPTION OF THE INVENTION

Unless otherwise indicated, the following terms as used throughout this specification have the following meanings:

"Me" refers to methyl.
"Et" refers to ethyl.
"tBu" refers to t-butyl.
"iPr" refers to i-propyl.
"Ph" refers to phenyl.
"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 2 to 12 carbons. More preferably it is a lower alkenyl of from 2 to 7 carbons, most preferably 2 to 4 carbons. The alkenyl group may be optionally substituted with one or more substituents selected from the group consisting of hydroxyl, cyano, alkoxy, O, S, $NO_2$, halogen, dimethyl amino, and SH.

"Alkynyl" refers to a straight-chain, branched or cyclic unsaturated hydrocarbon containing at least one carbon-carbon triple bond. Preferably, the alkynyl group has 2 to 12 carbons. More preferably it is a lower alkynyl of from 2 to 7 carbons, most preferably 1 to 4 carbons. The alkynyl group may be optionally substituted with one or more substituents selected from the group consisting of hydroxyl, cyano, alkoxy, O, S, $NO_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a —N(R")R''' group, wherein R" and R''' are independently selected from the group consisting of alkyl, aryl, and alkylaryl.

"Thioether" refers to —S—R", wherein R" is alkyl, aryl, or alkylaryl.

"Sulfonyl" refers to —S(O)₂—R"'', where R"'' is aryl, C(CN)=C-aryl, $CH_2$ CN, alkyaryl, sulfonamide, NH-alkyl, NH-alkylaryl, or NH-aryl.

Also, alternatively the substituent on the phenyl moiety, as shown below, is referred to as an o, m or p substituent or a 2, 3 or 4 substituent, respectively. (Obviously, the 5 substituent is also a m substituent and the 6 substituent is an o substituent.)

Specific compounds of the invention are reported in Table I, below.

These compounds may be assessed for their ability to activate or block activation of the human S1P3 receptor in T24 cells stably expressing the human S1P3 receptor as follows: Ten thousand cells/well are plated into 384-well poly-D-lysine coated plates one day prior to use. The growth media for the S1P3 receptor expressing cell line is McCoy's 5A medium supplemented with 10% charcoal-treated fetal bovine serum (FBS), 1% antibiotic-antimycotic and 400 µg/ml geneticin. On the day of the experiment, the cells are washed twice with Hank's Balanced Salt Solution supplemented with 20 mM HEPES (HBSS/Hepes buffer). The cells are then dye loaded with 2 uM Fluo-4 diluted in the HBSS/Hepes buffer with 1.25 mM Probenecid and incubated at 37° C. for 40 minutes. Extracellular dye is removed by washing the cell plates four times prior to placing the plates in the FLIPR (Fluorometric Imaging Plate Reader, Molecular Devices). Ligands are diluted in HBSS/Hepes buffer and prepared in 384-well microplates. The positive control, Sphingosine-1-Phosphate (S1P), is diluted in HBSS/Hepes buffer with 4 mg/ml fatty acid free bovine serum albumin. The FLIPR transfers 12.5 µl from the ligand microplate to the cell plate and takes fluorescent measurements for 75 seconds, taking readings every second, and then for 2.5 minutes, taking readings every 10 seconds. Drugs are tested over the concentration range of 0.61 nM to 10,000 nM. Data for $Ca^{+2}$ responses are obtained in arbitrary fluorescence units and not translated into $Ca^{+2}$ concentrations. $IC_{50}$ values are determined through a linear regression analysis using the Levenburg Marquardt algorithm. The compounds listed in Table 1, that are active at the S1P receptor, show % inhibition, as defined as percent of receptor activity induced by 5 nM sphingosine-1-phosphate that is inhibited by a test compound at the highest dose tested (10 µM), of from 33 to 100%.

TABLE 1

| Example Number | Structure |
|---|---|
| 5 | 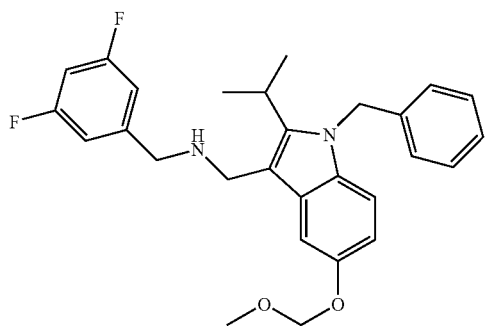 |
| 6 | 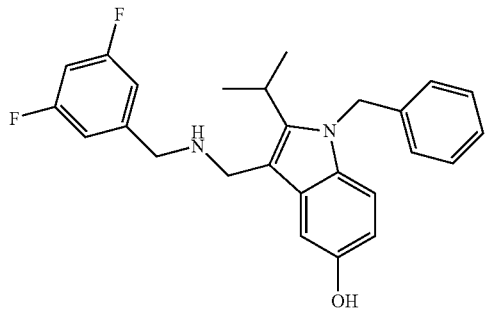 |
| 8 | 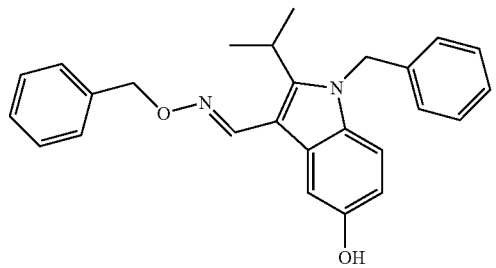 |

TABLE 1-continued

| Example Number | Structure |
|---|---|
| 10 | 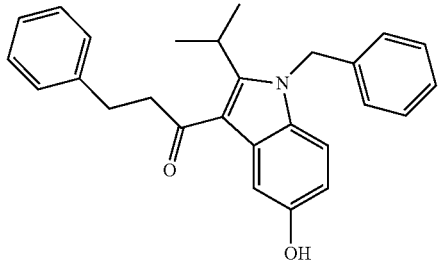 |
| 15 | 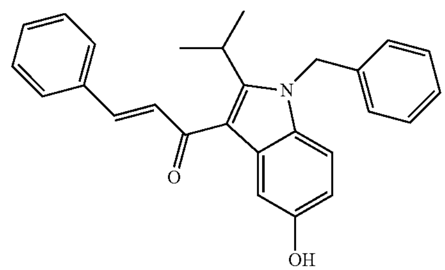 |
| 16 | 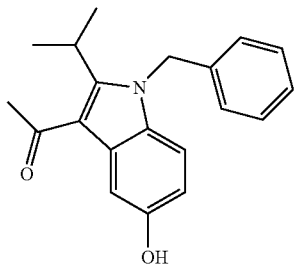 |
| 17 | 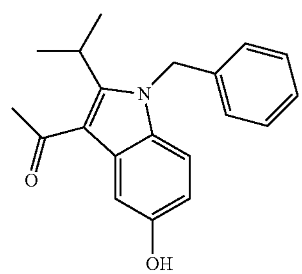 |
| 18 | 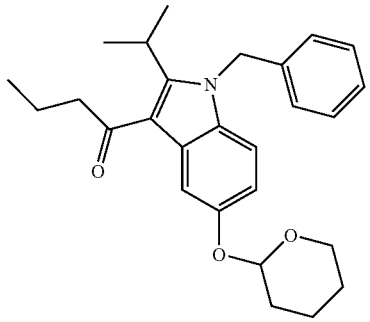 |

TABLE 1-continued
| Example Number | Structure |
|---|---|
| 19 | 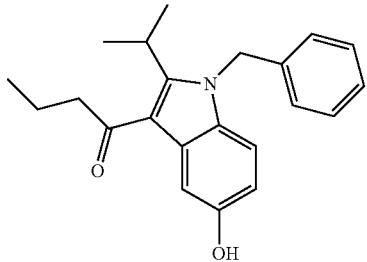 |
| 21 | 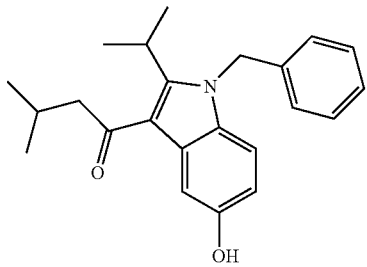 |
| 22 | 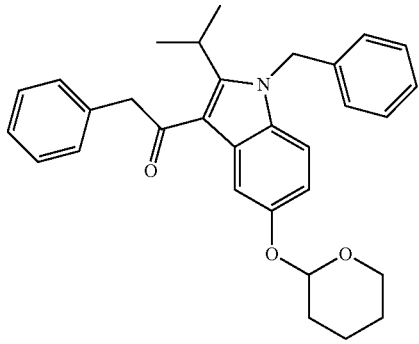 |
| 23 | 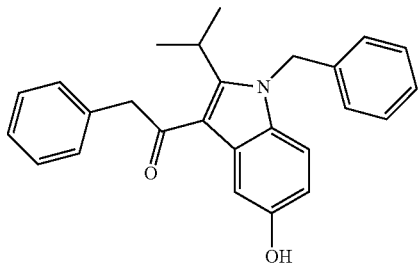 |
| 24 | 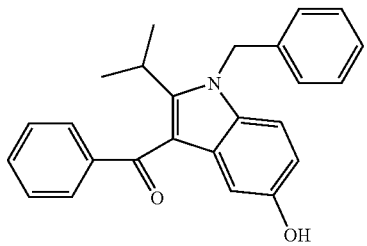 |
| 25 | 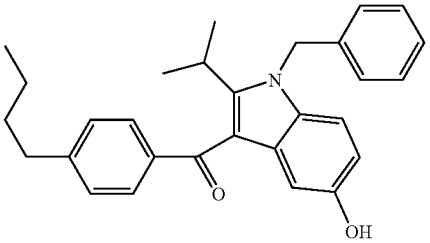 |
| 27 | 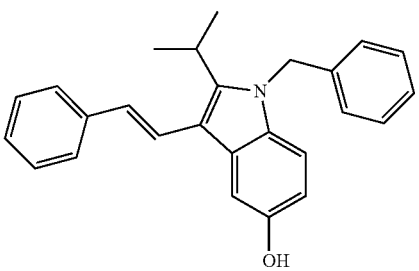 |
| 30 | 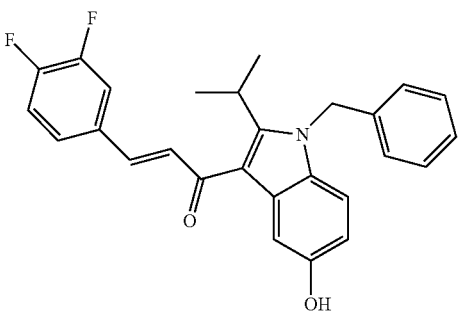 |
| 31 | 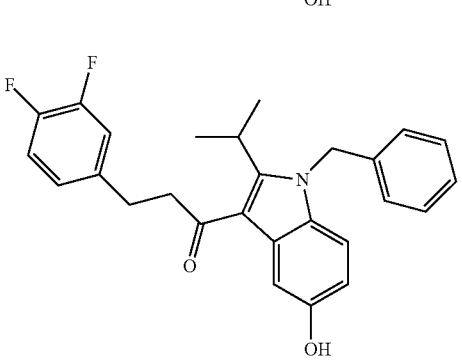 |
| 36 | 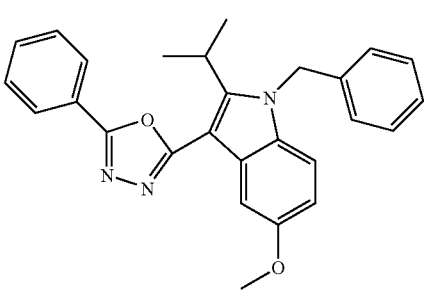 |

TABLE 1-continued

| Example Number | Structure |
|---|---|
| 43 | 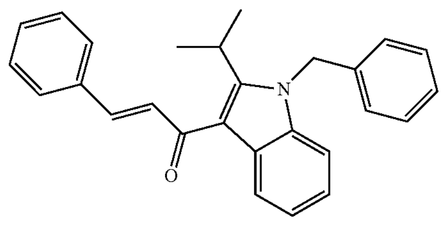 |
| 44 | 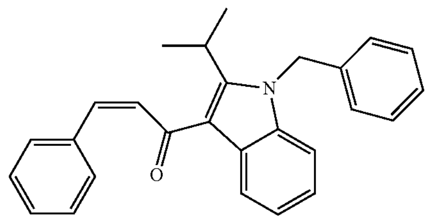 |
| 45 | 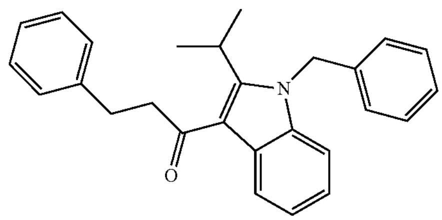 |
| 46 | 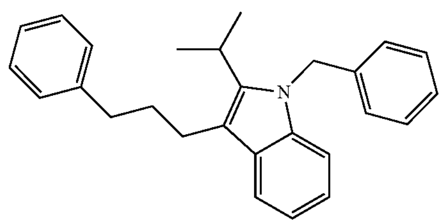 |
| 47 | 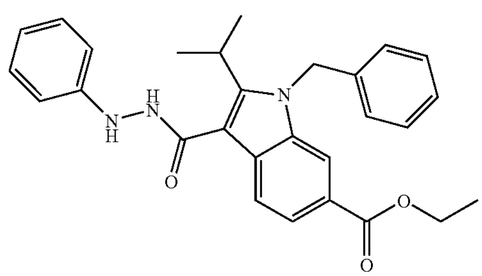 |
| 48 | 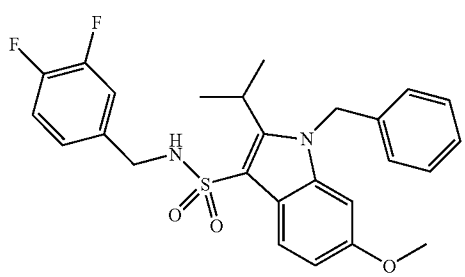 |

As a result of the above activity of the compounds utilized in the method of the present invention, it is clear that such compounds may be used in treating the following diseases and conditions for the following reasons.

Glaucoma
S1P1/3 subtypes expressed in primary HTM cells
S1P decreases outflow facility >30% in perfused porcine eyes (See IOVS 45, 2263; 2004)
    Altered paracellular permeability
Dry Eye/Immunology
Induces lymphocyte sequestration without affecting T cell proliferation
Angiogenesis Disorders
siRNA knockdown of S1P1 and S1P3 inhibits angiogenesis
    S1P1/3 subtypes expressed in VEC
        promote VEC migration
        promote barrier assembly and integrity
Cardiovascular (S1P3)
S1P3 "knock out" mice lack S1P induced COPD
S1P3 agonism is dose limiting effect of FTY720
Wound Healing
S1P is released from activated platelets Additional Clinical Potential of S1P Receptors Selective Agonist and Antagonist Ligands of the Invention S1P3 Blockage for Protecting Epithelial Integrity in Pulmonary Disease like Acute Respiratory Distress Syndrome Acute respiratory distress syndrome (ARDS) is a serious reaction to various forms of injuries to the lung. This is the most important disorder resulting in increased permeability pulmonary edema. The annual incidence of ARDS is between 1.5 to 13.5 people per 100,000 in the general population. Mechanical ventilation, sepsis, pneumonia, shock, aspiration, trauma (especially pulmonary contusion), major surgery, massive transfusions, smoke inhalation, drug reaction or overdose, fat emboli and reperfusion pulmonary edema after lung transplantation or pulmonary embolectomy may all trigger ARDS. Pneumonia and sepsis are the most common triggers, and pneumonia is present in up to 60% of patients. Pneumonia and sepsis may be either causes or complications of ARDS. It is hard to find a good method to treat ARDS in clinic. The most reliable treatment is ventilation with positive end-exporatory pressure (PEEP).

Pulmonary pathologies including adult respiratory distress syndrome are characterized by disruption of pulmonary integrity and edema compromising respiratory function. Sphingosine 1-phosphate (S1P) is a lipid mediator synthesized and/or stored in mast cells, platelets, and epithelial cells, with production up-regulated by the proinflammatory cytokines IL-1 and TNF. S1P administration via the airways but not via the vasculature induces lung leakage. Using receptor-null mice, results show that S1P, acting on $S1P_3$ receptor expressed on both type I and type II alveolar epithelial cells but not vascular endothelium, induces pulmonary edema by acute tight junction opening. WT but not $S1P_3$-null mice showed disruption of pulmonary epithelial tight junctions and the appearance of paracellular gaps between epithelial cells by electron microscopy within 1 h of airways exposure to S1P. S1P shows synergistic activity with the proinflammatory cytokine TNF, showing both pulmonary edema and mortality at subthreshold S1P doses. Specifically, preexposure of mice to subthreshold doses of TNF, which alone induced no lung edema, exacerbated S1P-induced edema and impaired survival. S1P, acting through $S1P_3$, regulates epithelial integrity and acts additively with TNF in compromising respiratory barrier function. Because $S1P_3$-null mice are resistant to S1P-induced pulmonary leakage, either alone or in the presence of TNF, S1P$_3$ antagonism may be useful in protecting epithelial integrity in pulmonary disease.

Based on the data that show S1P, acting through the S1P3 receptor expressed on pulmonary epithelium, is an acute regulator of epithelial integrity by disrupting tight junctions. S1P3 blockers are believed to be useful for treating ARDS.

Regulation of S1P Signaling EDG Receptor Pathway to Improve the Condition of Congestive Cardiac Failure Congestive heart failure (CHF), also called congestive cardiac failure (CCF) or just heart failure, is a condition that can result from any structural or functional cardiac disorder that impairs the ability of the heart to fill with or pump a sufficient amount of blood throughout the body. The most common cause of heart failure is ischemic heart disease (myocardial infarction of coronary artery disease). Left heart failure will increase hypertension in pulmonary system, and fail to remove the fluid from the lung circulation to lead pulmonar edema.

There is a vicious circle in left heart failure and lung edema. Heart ischemia and infarction reduce myocarial contraction to induce heart failure, pulmonary hepertension, and pulmonary edema. Pulmonary edema inrease barrier of oxygen from lung to blood of lung circulation, then Po2 in artery will sharply decrease. The supplement of oxygen to heart will short to requirement for keeping contraction force, then enforce heart failure.

The most common cause of CHF in United States is ischemic heart disease. The treatment of CHF in clinic includes improving heart function, reducing heart preload and afterload. Research demonstrated that S1P signaling Edg receptor pathway may be involved in regulation of cardiovascular systems and pulmonary leakage. S1P acutely protect the heart against ischemia/reperfusion injury, decrease the region of infarction of myocardial ischemia, and keep coronary artery in dilation. S1P also can enhance pulmonary endothelial cell barrier to reduce lung edema that was induced by left heart failure. Antagonist of S1P3 receptor can block contraction of vascular smooth muscle, and decrease heart afterload. Blockage of S1P3 receptor also can prevent one of S1P toxicity, bradycardia.

Treatment of Asthma and Chronic Obstructive Pulmonary Disease

Asthma is a chronic disease of the respiratory system in which the airway occasionally constricts, becomes inflamed, and is lined with excessive amounts of mucus, often in response to one or more triggers. In response to exposure to these triggers, the bronchi contract into spasm (an "asthma attack"). Inflammation soon follows, leading to a further narrowing of the airways and excessive mucus production, which leads to coughing and other breathing difficulties.

Chronic obstructive pulmonary disease (COPD) belongs next to bronchial asthma to the most important diseases of the respiratory tract. COPD is a major global health problem, and is predicted to become the third most common cause of death by 2020. COPD is a disease characterized by progressive airflow obstruction of the peripheral airways, associated with lung inflammation, emphysema and mucus hypersecretion.

The major problems in asthma and COPD are bronchi or small bronchi constriction, and inflamation. Recently, many science papers reported S1P involved in constrction of human airway smooth muscle cells. S1P stimulates constrction of human airway smooth muscle cells by S1P3 receptors. Recent work has revealed that levels of S1P are elevated in the airways of asthmatics and not in healthy individuals after segmental allergan challenge. Research also demonstrates that S1P signaling pathway contributes to cholinergic constriction of murine peripherial airways.

Thus, S1P3 receptor is a potential new therapeutic target for asthma and COPD. S1P3 antagonist would block the stimulation of S1P to human airway smooth muscle cell S1P3 receptor preventing bronchial constraction.

Use of S1P3 Receptor Selective Antagonist in Controlling Human Hypertension

Hypertension, commonly referred to as "high blood pressure", is a medical condition where the blood pressure is chronically elevated. Persistent hypertension is one of the risk factors for strokes, heart attacks, heart failure and arterial aneurysm, and is a leading cause of chronic renal failure. Currently, it is estimated that 58 million adults in the United States have hypertension or are taking antihypertensive medications. In addition to definitive hypertension, an additional 45 million adults in the United States have pre-hypertension.

Recently, it has been found that S1P, a bioactive lipid mediator, involved in cardiovascular system, and cholesterol metabolism. Evidences link S1P$_3$ receptor activity with acute toxicity and cardiovascular regulation: compound potency on S1P$_3$ correlated with toxicity and bradycardia; the shift in potency of phosphorylated-FTY720 for inducing lymphopenia versus bradycardia and hypertension was consistent with affinity for S1P$_1$ relative to S1P$_3$; and toxicity, bradycardia, and hypertension were absent in S1P3$^{-/-}$ mice. Blood pressure effects of agonists in anesthetized rats were complex, whereas hypertension was the predominant effect in conscious rats and mice. Immunolocalization of S1P$_3$ in rodent heart revealed abundant expression on myocytes and perivascular smooth muscle cells consistent with regulation of bradycardia and hypertension, whereas S1P$_1$ expression was restricted to the vascular endothelium. In conclusion, hypertension is clearly associated with S1P3 activation and its expression patterns in cardiovascular tissue. S1P and S1P3 receptor is believe to play an important role in the regulation of blood pressure.

Heart Rate Regulation of S1P3 Signaling Pathway May be Used for Controlling Techycardia, One of Most Common Cardiac Arrithymias Tachycardia refers to a rapid beating of the heart. By convention the term refers to heart rates greater than 100 beats per minute in the adult patient. Tachycardia may be a perfectly normal physiological response to stress. However, depending on the mechanism of the tachycardia and the health status of the patient, tachycardia may be harmful, and require medical treatment. In extreme cases, tachycardia can be life threatening.

Tachycardia can be harmful in two ways. First, when the heart beats too rapidly, it may perform inefficiently. Second, the faster the heart beats, the more oxygen and nutrients the heart requires. This can be especially problematic for patients suffering from ischemic heart disease.

Sphingosine 1-phosphate (S1P) influences heart rate, coronary artery caliber, endothelial integrity, and lymphocyte recirculation through five related high affinity G-protein-coupled receptors. Circumstantial evidence largely from cultured atrial myocytes and using suramin inhibition as a measure of S1P$_3$ function has postulated a role for S1P$_3$ in the activation of an I$_{KAch}$ channel-inducing bradycardia. The demonstration in vivo that a non-selective S1P receptor agonist active on S1P$_3$ induces bradycardia in wild-type mice that is abolished in S1P$_3$–/– provides further support for the role of S1P$_3$ in the heart. Both S1P$_1$ and S1P$_3$ are expressed on cardiac endothelium and perhaps myocardium, yet deletion of S1P$_3$ alone abolishes the bradycardia induced by non-selective S1P receptor agonists, and an S1P$_1$-selective agonist does not induce bradycardia. The sphingolipid drug FTY720 displays structural similarity to S1P and efficacy as an immunosuppressant in models of autoimmune disease and in solid organ transplantation. While FTY720 is well-tolerated in humans, it produces a transient reduction of heart rate (HR). As S1P activates the cardiac G protein-gated potassium channel IKACh, FTY720-induced HR reduction reflects IKACh activation. In wild-type myocytes, the active phosphate metabolite of FTY720 (FTY720-P) induced single channel activity with conductance, open time, GTP sensitivity and rectification identical to that of IKACh. In whole-cell recordings, FTY720-P evoked an inwardly rectifying potassium current in ~90% of myocytes responding to acetylcholine. Comparable channel activity was never observed in myocytes from IKACh-deficient mice. In wild-type mice, acute FTY720 administration produced a dose-dependent, robust HR reduction. In contrast, the HR reduction induced by FTY720 in IKACh-deficient mice was blunted. Research concludes that the effect of acute FTY720 administration on HR is mediated primarily by IKACh activation.

Clinical Potential of S1P Signaling EDG Receptors Pathway in Protecting Myocardial Ischemia and Reperfusion Injury myocardial infarction, commonly known as a heart attack, is a disease state that occurs when the blood supply to a part of the heart is interrupted. The resulting oxygen shortage causes damage and potential death of heart tissue. It is a medical emergency, and the leading cause of death for both men and women all over the world. The main therapeutic goals in patients with acute myocardial infarction are to minimize myocardial damage, improve cardiac repair, and reduce myocardial remodeling. State-of-the-art therapy is rapid reperfusion of the infarcted myocardium through revascularization of the occluded vessel. However, the benefit of reperfusion is compromised by the endothelial injury and inflammation that follow reinstitution of blood flow, leading to additional myocardial damage, a process termed "ischemia/referfusion injury." Despite all efforts to prevent the sequelae of referfusion injury in patients, there are currently no clinical strategies available to effectively protect cardiac tissue from the inflammatory damage inherent reperfusion.

S1P is a bioactive phospholipid that is primarily stored in platelets. Platelets play a key role in the response to acute vascular injury. S1P potently affects the development and function of the heart. Mutation in a zebrafish S1P receptor called Miles Apart (which is most similar to the $S1P_2$ receptor of mammals) results in a myocardial precursor cell migration defect and formation of the cardia bifida condition, wherein the two primitive heart tube structures fail to coalesce and form a single mature heart structure. Studies in adult cardiac cells showed that S1P regulates the calcium metabolism and ionic currents in cells of the sinoatrial node, which controls heart rate. In addition, S1P was shown to prevent death of cardiac myocytes on ischemia/reperfusion injury. Cardiomyocytes express $S1P_{1-3}$ receptors, suggesting that signaling pathways stimulated by these receptors may contribute to intrinsic myocardial function. In an animal model of ischemia/reperfusion injury of the heart, S1P was found to be cardioprotective. In a mouse model of myocardial ischemia/reperfusion, S1P dramatically attenuated infarction size by approximately 20% and 40%, respectively. The underlying mechanism was an inhibition of inflammatory neutrophil recruitment and cardiomyocyte apoptosis in the infarcted area. S1P potently suppressed leukocyte adhesion to activated endothelium under flow and protected rat neonatal cardiomyocytes against apoptosis.

The invention is further illustrated by the following examples which are illustrative of a specific mode of practicing the invention and are not intended as limiting the scope of the claims.

Unless otherwise indicated, the following Chemical Abbreviations are used in the examples:
HCl: hydrogen chloride or hydrochloric acid
NaOH: sodium hydroxide
KOH: potassium hydroxide
$Na_2SO_4$: sodium sulfate
$NaHCO_3$: sodium bicarbonate
$MgSO_4$: magnesium sulfate
MeOH: methanol
EtOH: ethanol
i-PrOH: isopropanol
EtOAc: ethyl acetate
$Et_2O$: diethyl ether
$CH_2Cl_2$: methylene chloride
DMF: N,N-dimethylformamide
DMSO: dimethylsulfoxide
DHP: dihydropyran
LDA: lithium diisopropylamide
$LiAlH_4$: lithium aluminum hydride
MOMCl: methyl chloromethyl ether
MeLi: methyllithium
MeMgBr: Methylmagnesium bromide
$NaBH_3CN$: sodium cyanoborohydride
NMO: 4-methylmorpholine, N-oxide
Pd—C: palladium on activated carbon
PhCHO: benzaldehyde
THF: tetrahydrofuran
THP: tetrahydropyran
TPAP: tetrapropylammonium perruthenate
PTLC: preparative thin layer chromatography Benzylamine, benzylmagnesium bromide, butylmagnesium bromide, 4-butylphenylmagnesium bromide, 3,4-difluorobenzaldehyde, 3,5-difluorobenzylamine, ethyl isobutyrylacetate, O-benzyl oxime, O-phenylhydroylamine hydrochloride, 3-methylbutylmagnesium bromide, and 2-phenylethylmagnesium bromide were purchased from Aldrich Chemical Company.

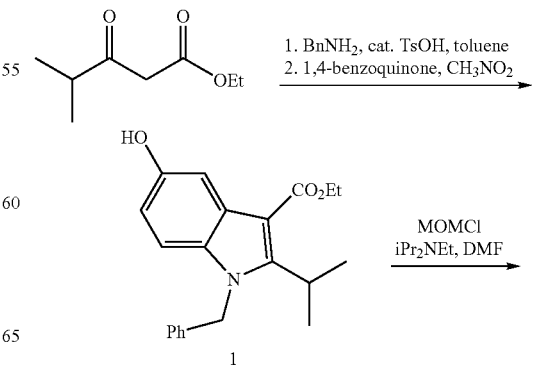

SCHEME 4

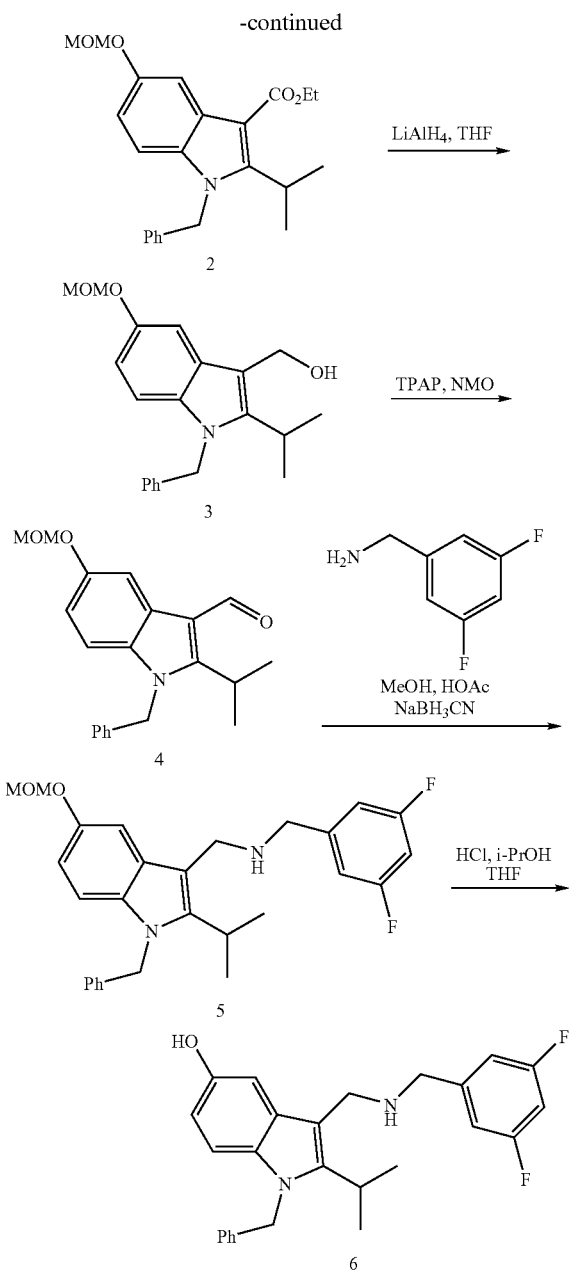

Example 1

1-Benzyl-5-hydroxy-2-isopropyl-1H-indole-3-carboxylic Acid, Ethyl ester (Compound 1). General Procedure A. To a solution of ethyl isobutyrylacetate (3.0 g, 19.0 mmol) and benzylamine (2.2 ml, 19.9 mmol) in toluene (30 ml) was added p-toluenesulfonic acid monohydrate (p-TsOH, 181 mg, 1.0 mmol). The mixture was heated at 140° C. to reflux for 4 h, cooled to 0° C. and filtered. The filtrate was concentrated under reduced pressure to give a yellow oil (4.3 g). To a solution of 1,4-benzoquinone (3.1 g, 28.5 mmol) in nitromethane (16 ml) was added a solution of the above yellow oil in nitromethane (8 ml) slowly. The resulting mixture was stirred at room temperature for 18 h and was cooled to 0° C. and filtered, the filtrate was concentrated and purified by flash chromatography on silica gel eluting with 20% EtOAc-hexanes to yield 1-benzyl-5-hydroxy-2-isopropyl-1H-indole-3-carboxylic acid, ethyl ester (Compound 1) as a brown solid.

$^1$H NMR (CD$_3$OD) δ 1.34 (d, J=7.0 Hz, 6H), 1.47 (t, J=7.0 Hz, 3H), 3.78-3.96 (m, 1H), 4.37 (q, J=7.1 Hz, 2H), 5.51 (s, 2H), 6.68 (dd, J=8.8, 2.3 Hz, 2H), 6.90-6.99 (m, 2H), 7.08 (d, J=8.8 Hz, 1H), 7.18-7.33 (m, 3H), 7.56 (d, J=2.1 Hz, 1H).

Example 2

1-Benzyl-2-isopropyl-5-(methoxymethoxy)-1H-indole-3-carboxylic Acid (Compound 2). To a solution of 1-benzyl-5-hydroxy-2-isopropyl-1H-indole-3-carboxylic acid, ethyl ester (Compound 1, 345 mg, 1.0 mmol) in DMF (2 ml) was added diisopropylethylamine (iPr$_2$NEt, 1.7 ml, 10.0 mmol) and chloromethyl methyl ether (MOMCl, 0.38 ml, 5.0 mmol). The mixture was stirred at room temperature for 72 h, and concentrated under vacuum, and purified by flash chromatography on silica gel eluting with 10-20% EtOAc-hexanes to yield 1-benzyl-2-isopropyl-5-(methoxymethoxy)-1H-indole-3-carboxylic acid, ethyl ester (Compound 2) as a clear oil.

$^1$H NMR (CDCl$_3$) δ 1.37 (d, J=7.3 Hz, 6H), 1.48 (t, J=7.2 Hz, 3H), 3.52 (s, 3H), 3.90-4.07 (m, 1H), 4.41 (q, J=7.1 Hz, 2H), 5.21 (s, 2H), 5.45 (s, 2H), 6.89 (dd, J=8.8, 2.3 Hz, 1H), 6.95 (dd, J=7.9, 1.8 Hz, 2H), 7.04 (d, J=8.8 Hz, 1H), 7.21-7.32 (m, 3H), 7.88 (d, J=2.6 Hz, 1H).

Example 3

(1-Benzyl-2-isopropyl-5-(methoxymethoxy)-1H-indol-3-yl)methanol (Compound 3). To a solution of lithium aluminum hydride (LiAlH$_4$, 144 mg, 3.6 mmol) in THF (10 ml) at 0° C. was added 1-benzyl-2-isopropyl-5-(methoxymethoxy)-1H-indole-3-carboxylic acid, ethyl ester (Compound 2, 270 mg, 0.71 mmol) in THF (5 ml) slowly. The reaction was stirred at room temperature for 4.5 h, cooled to 0° C., and it was quenched with H$_2$O (0.7 ml) and 4 M NaOH (1.0 ml), Silica gel was added, and the mixture was diluted with EtOAc, and filtered through Celite, and it was concentrated to yield the crude product, (1-benzyl-2-isopropyl-5-(methoxymethoxy)-1H-indol-3-yl)methanol (Compound 3) as a clear oil, which was used immediately in the next step (Example 4) without further purification or characterization.

Example 4

1-Benzyl-2-isopropyl-5-(methoxymethoxy)-1H-indole-3-carboxaldehyde (Compound 4). General Procedure B. To a solution of (1-benzyl-2-isopropyl-5-(methoxymethoxy)-1H-indol-3-yl)methanol (Compound 3, 120 mg, 0.35 mmol) in CH$_2$Cl$_2$ was added 4-methylmorpholine N-oxide (NMO, 129 mg, 1.1 mmol) and tetrapropylammonium perruthenate (TPAP, 14 mg, 0.040 mmol). The reaction was stirred at room temperature for 2.5 h, and the product was purified by flash chromatography on silica gel eluting with 20% EtOAc-hexanes to yield 1-benzyl-2-isopropyl-5-(methoxymethoxy)-1H-indole-3-carboxaldehyde (Compound 4) as an off-white solid.

$^1$H NMR (CDCl$_3$) δ 1.44 (d, J=7.0 Hz, 6H), 3.39-3.55 (m, 1H), 3.51 (s, 3H), 5.24 (s, 2H), 5.41 (s, 2H), 6.93-7.02 (m, 3H), 7.09-7.14 (d, J=8.8 Hz, 1H), 7.23-7.35 (m, 3H), 8.06 (d, J=2.6 Hz, 1H), 10.43 (s, 3H).

Example 5

1-(1-Benzyl-2-isopropyl-5-(methoxymethoxy)-1H-indol-3-yl)-N-(3,5-difluorobenzyl)methanamine (Compound 5).

To a solution of 1-benzyl-2-isopropyl-5-(methoxymethoxy)-1H-indole-3-carboxaldehyde (Compound 4, 103 mg, 0.31 mmol) in methanol (5.0 ml) was added 3,5-difluorobenzylamine (49 μl, 0.40 mmol), and acetic acid (2 drops). After stirring at room temperature for 1 h, sodium cyanoborohydride (29 mg, 0.47 mmol) was added and the reaction was stirred for 5 h. More 3,5-difluorobenzylamine (50 μl, 0.40 mmol) was added, and the reaction was stirred for 64 h. The solvent was removed and the crude reaction mixture was purified by flash chromatography on silica gel eluting with 10-50% EtOAc-hexanes to yield 1-(1-benzyl-2-isopropyl-5-(methoxymethoxy)-1H-indol-3-yl)-N-(3,5-difluorobenzyl)methanamine (Compound 5) as a light greenish yellow oil.

$^1$H NMR (CDCl$_3$) δ 1.30 (d, J=7.3 Hz, 6H), 3.12-3.30 (m, 1H), 3.53 (s, 3H), 3.89 (s, 2H), 4.00 (s, 2H), 5.20 (s, 2H), 5.35 (s, 2H), 6.63-6.73 (m, 1H), 6.85 (dd, J=8.8, 2.3 Hz, 1H), 6.90-6.99 (m, 4H), 7.02 (d, J=8.8 Hz, 1H), 7.20-7.31 (m, 4H).

Example 6

1-Benzyl-3-((3,5-difluorobenzylamino)methyl)-2-isopropyl-1H-indol-5-ol (Compound 6). To a solution of 1-(1-benzyl-2-isopropyl-5-(methoxymethoxy)-1H-indol-3-yl)-N-(3,5-difluorobenzyl)methanamine (Compound 5, 117 mg, 0.25 mmol) in isopropanol (2.0 ml) and THF (2.0 ml) was added 6 M HCl (0.4 ml). The mixture was stirred at room temperature for 16 h, and concentrated under vacuum. The mixture was diluted with EtOAc, and washed with phosphate buffer (pH=7.2), and brine, and dried over Na$_2$SO$_4$, and concentrated under vacuum. The residue was purified by flash chromatography on silica gel eluting with 20-60% EtOAc-hexanes to yield 1-benzyl-3-((3,5-difluorobenzylamino)methyl)-2-isopropyl-1H-indol-5-ol (Compound 6) as a yellow solid.

$^1$H NMR (CDCl$_3$) δ 1.30 (d, J=7.3 Hz, 6H), 3.15-3.27 (m, 1H), 3.87 (s, 2H), 3.98 (s, 2H), 5.35 (s, 2H), 6.64-6.73 (m, 2H), 6.93 (d, J=6.8 Hz, 4H), 6.97 (d, J=8.8 Hz, 1H), 7.03 (d, J=2.4 Hz, 1H), 7.18-7.28 (m, 3H).

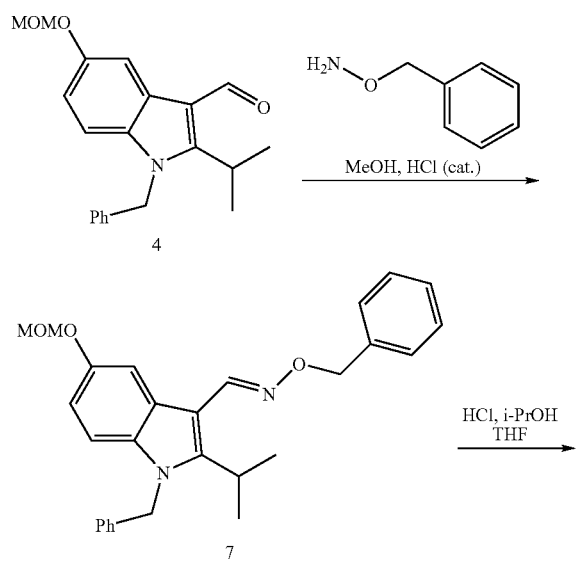

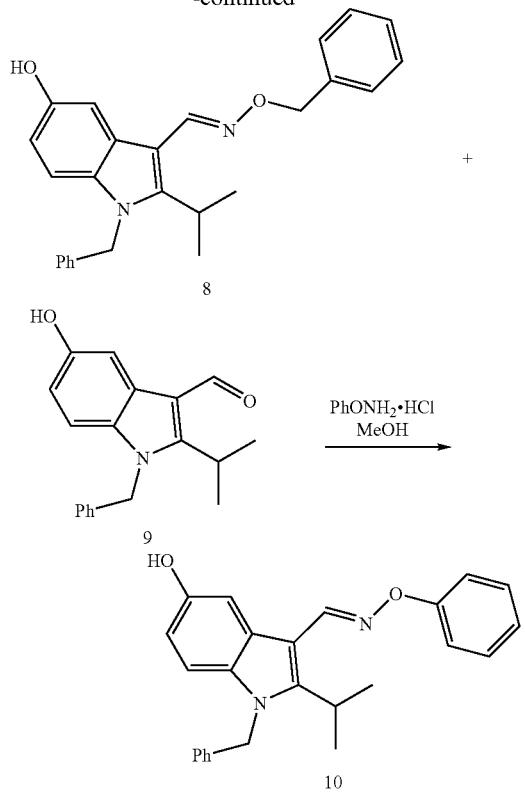

Example 7

(E)-1-Benzyl-2-isopropyl-5-(methoxymethoxy)-1H-indole-3-carboxaldehyde, O-Benzyl Oxime (Compound 7). To a solution of 1-benzyl-2-isopropyl-5-(methoxymethoxy)-1H-indole-3-carboxaldehyde (Compound 4, 43 mg, 0.13 mmol) in methanol (2.0 ml) was added O-benzylhydroxylamine (16 mg, 0.13 mmol) and 1 M HCl (1 drop). After stirring at room temperature for 64 h, the solvent was removed and the crude reaction mixture was purified by flash chromatography on silica gel eluting with 0-30% EtOAc-hexanes to yield (E)-1-benzyl-2-isopropyl-5-(methoxymethoxy)-1H-indole-3-carboxaldehyde O-benzyl oxime (Compound 7) as a clear oil.

$^1$H NMR (CDCl$_3$) δ 1.34 (d, J=7.3 Hz, 6H), 3.22-3.33 (m, 1H), 3.56 (s, 3H), 5.24 (s, 2H), 5.28 (s, 2H), 5.39 (s, 2H), 6.93-7.01 (m, 3H), 7.09 (d, J=8.8 Hz, 1H), 7.23-7.32 (m, 3H), 7.36 (d, J=7.3Hz, 1H), 7.42 (t, J=7.3 Hz, 2H), 7.56 (d, J=7.3 Hz, 2H), 7.96 (d, J=2.4 Hz, 1H), 8.69 (s, 1H).

Example 8

(E)-1-Benzyl-5-hydroxy-2-isopropyl-1H-indole-3-carboxaldehyde, O-Benzyl Oxime (Compound 8). To a solution of (E)-1-benzyl-2-isopropyl-5-(methoxymethoxy)-1H-indole-3-carboxaldehyde, O-benzyl oxime (Compound 7, 57 mg, 0.13 mmol) in isopropanol (2.0 ml) and THF (2.0 ml) was added 6 M HCl (0.22 ml). The mixture was stirred at room temperature for 20 h, diluted with EtOAc, washed with brine, dried over Na$_2$SO$_4$, and concentrated. The residue was purified by flash chromatography on silica gel eluting with 0-50% EtOAc-hexanes to yield (E)-1-benzyl-5-hydroxy-2-isopropyl-1H-indole-3-carboxaldehyde O-benzyl oxime (Compound 8) as a clear film.

$^1$H NMR (CDCl$_3$) δ 1.34 (d, J=7.3 Hz, 6H), 3.21-3.32 (m, 1H), 5.29 (s, 2H), 5.38 (s, 2H), 6.77 (dd, J=8.8, 2.4 Hz, 1H), 6.96 (d, J=6.3 Hz, 2H), 7.04 (d, J=8.3 Hz, 1H), 7.23-7.32 (m, 3H), 7.36 (t, J=7.3 Hz, 1H), 7.43 (t, J=7.6 Hz, 2H), 7.54 (d, J=7.8 Hz, 2H), 7.67 (d, J=2.4 Hz, 1H), 8.69 (s, 1H).

Example 9

1-Benzyl-5-hydroxy-2-isopropyl-1H-indole-3-carboxaldehyde (Compound 9). The title compound was isolated as a bi-product in the synthesis of Compound 8.

$^1$H NMR (CDCl$_3$) δ 1.47 (d, J=7.3 Hz, 6H), 3.40-3.51 (m, 1H), 5.43 (s, 2H), 6.90 (dd, J=8.8, 2.4 Hz, 1H), 7.02 (d, J=6.8 Hz, 2H), 7.11 (d, J=8.8 Hz, 1H), 7.27-7.35 (m, 3H), 8.43 (d, J=2.4 Hz, 1H), 10.39 (s, 1H).

Example 10

(E)-1-Benzyl-5-hydroxy-2-isopropyl-1H-indole-3-carbaldehyde, O-Phenyl Oxime (Compound 10). To a solution of 1-benzyl-5-hydroxy-2-isopropyl-1H-indole-3-carboxaldehyde (Compound 9, 16 mg, 0.055 mmol) in methanol (1.0 ml) was added O-phenylhydroxylamine hydrochloride (8 mg, 0.055 mmol). After stirring the solution at room temperature for 1 h, the solvent was removed under vacuum and the crude reaction mixture was purified by flash chromatography on silica gel eluting with 0-20% EtOAc-hexanes to yield (E)-1-benzyl-5-hydroxy-2-isopropyl-1H-indole-3-carboxaldehyde, O-phenyl oxime (Compound 10) as an off-white solid.

$^1$H NMR (CDCl$_3$) δ 1.42 (d, J=7.3 Hz, 6H), 3.29-3.41 (m, 1H), 5.42 (s, 2H), 6.82 (dd, J=8.5, 2.7 Hz, 1H), 7.00 (d, J=6.8 Hz, 2H), 7.06 (t, J=7.1 Hz, 1H), 7.10 (d, J=8.8 Hz, 1H), 7.26-7.43 (m, 7H), 7.83 (d, J=2.4 Hz, 1H), 8.97 (s, 1H).

SCHEME 6

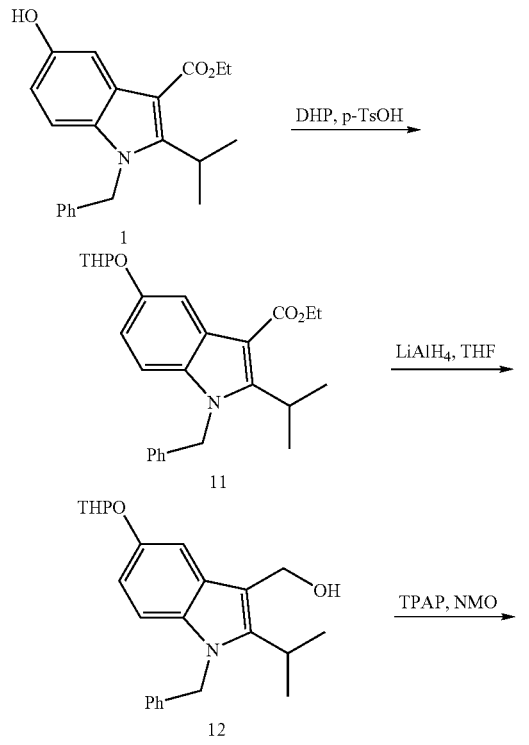

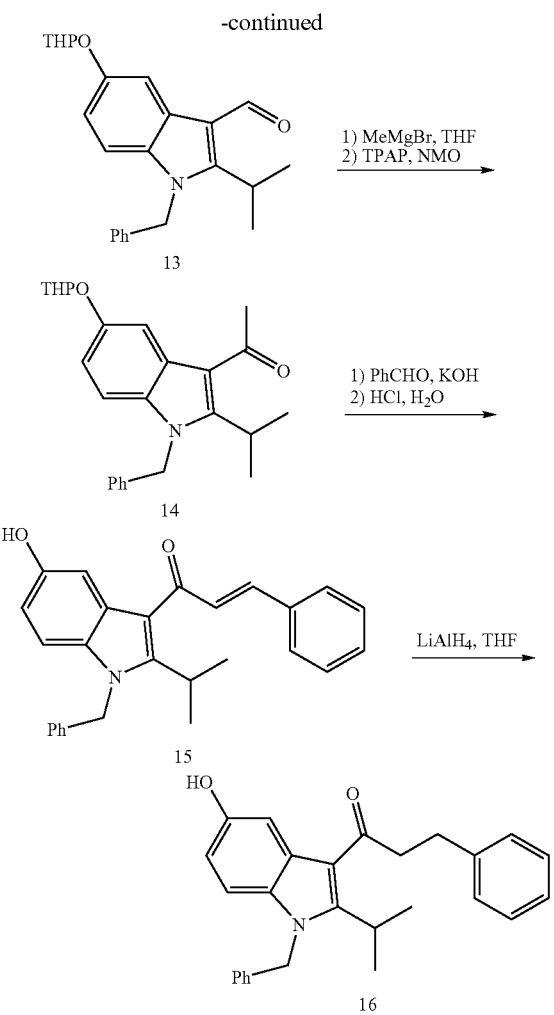

Example 11

1-Benzyl-2-isopropyl-5-(tetrahydropyran-2-yloxy)-1H-indole-3-carboxylic Acid, Ethyl Ester (Compound 11). To a cold (0° C.) solution of 1-benzyl-5-hydroxy-2-isopropyl-1H-indole-3-carboxylic acid, ethyl ester (Compound 1, 2.3 gm, 6.82 mmol) in CH$_2$Cl$_2$ (31 mL) was added dihydropyran (DHP, 3.1 g, 36.9 mmol) and p-TsOH (50 mg). The cooling bath was removed, and the solution was stirred at ambient temperature for 16 h. The reaction was quenched by adding aqueous NaHCO$_3$ (20 mL) and CH$_2$Cl$_2$ (50 mL). The layers were separated, and the organic layer was washed with brine (20 mL), and dried (MgSO$_4$), and solvent removed under vacuum. The crude mixture was purified by silica gel flash chromatography by eluting with 10% EtOAc in hexanes to isolate 1-benzyl-2-isopropyl-5-(tetrahydropyran-2-yloxy)-1H-indole-3-carboxylic acid, ethyl ester (Compound 11) as a thick pale yellow oil.

$^1$H NMR (CDCl$_3$) δ 1.33 (d, J=7.3 Hz, 6H), 1.45 (t, J=7.3 Hz, 3H), 1.60-1.80 (br m, 4H), 1.91 (m, 1H), 2.02 (m, 1H), 3.61 (m, 1H), 4.00 (m, 2H), 4.42 (q, J=7.3 Hz, 2H), 5.40 (t, J=1.6 Hz, 1H), 5.44 (s, 2H), 6.90 (dd, J=2.0, 7.2 Hz, 1H), 6.95 (d, J=7.5 Hz, 2H), 7.01 (d, J=7.2 Hz, 1H), 7.25 (m, 3H), 7.85 (1H, J=2.0 Hz, 1H).

Example 12

(1-Benzyl-2-isopropyl-5-(tetrahydropyran-2-yloxy)-1H-indol-3-yl)methanol (Compound 12). To −78° C. solution of 1-benzyl-2-isopropyl-5-(tetrahydropyran-2-yloxy)-1H-indole-3-carboxylic acid, ethyl ester (Compound 11, 2.11 g, 5 mmol) in THF (30 mL) was added a 1 M solution of LiAlH$_4$ in THF (9 mL, 9 mmol) dropwise over 5 minutes. The mixture was gradually warmed to 0° C. over 4 h. The reaction was cooled to −78° C. and quenched by adding EtOAc (5 mL) and saturated aqueous Na$_2$SO$_4$ (9 mL). The solution was warmed to room temperature and stirred for 20 minutes. The resulting precipitate was filtered off, and the organic layer was dried (Na$_2$SO$_4$). The solvent was removed under vacuum to obtain (1-benzyl-2-isopropyl-5-(tetrahydropyran-2-yloxy)-1H-indol-3-yl)methanol (Compound 12) as a white solid.

$^1$H NMR (CDCl$_3$) δ 1.35 (d, J=7.5 Hz, 6H), 1.60-1.80 (br m, 4H), 1.91 (m, 1H), 2.02 (m, 1H), 3.23 (m, 1H), 3.75 (m, 1H), 4.00 (m, 1H), 4.90 (s, 2H), 5.36 (s, 2H), 5.40 (t, J=1.6 Hz, 1H), 6.90 (dd, J=2.0, 7.2 Hz, 1H), 6.95 (d, J=7.5 Hz, 2H), 7.05 (d, J=7.2 Hz, 1H), 7.25 (m, 3H), 7.40 (1H, J=2.0 Hz, 1H).

Example 13

(1-Benzyl-2-isopropyl-5-(tetrahydropyran-2-yloxy)-1H-indole-3-carboxaldehyde (Compound 13). The title compound was prepared from (1-benzyl-2-isopropyl-5-(tetrahydropyran-2-yloxy)-1H-indol-3-yl)methanol (Compound 12) by General Procedure B.

$^1$H NMR (CDCl$_3$) δ 1.43 (d, J=7.3 Hz, 6H), 1.60-1.75 (br m, 4H), 1.95 (m, 1H), 2.10 (m, 1H), 3.45 (m, 1H), 3.61 (m, 1H), 3.95 (m, 1H), 5.47 (s, 2H), 5.48 (t, J=3 Hz, 1H), 6.90 (m, 3H), 7.10 (d, J=8.5Hz, 1H), 7.27 (m, 3H), 8.07 (d, J=3.0 Hz, 1H), 10.43 (s, 1H).

Example 14

1-(1-Benzyl-2-isopropyl-5-(tetrahydropyran-2-yloxy)-1H-indol-3-yl)ethanone (Compound 14). General Procedure C. To a −78° C. solution of (1-benzyl-2-isopropyl-5-(tetrahydropyran-2-yloxy)-1H-indole-3-carboxaldehyde (Compound 13, 200 mg, 0.55 mmol) in THF (5 mL) was added MeMgBr (3 M solution in THF, 1 mL, 3 mmol). The solution was stirred between −78° C. and −10° C. for 4 h, and then the reaction was quenched at −78° C. by adding EtOAc (2 mL) and water (5 mL). The mixture was warmed to room temperature and diluted with EtOAc (50 mL). The reaction was quickly washed with ice cold aqueous NH$_4$Cl (5 mL), and brine (10 mL), and dried (Na$_2$SO$_4$), and the solvent was removed under vacuum to give 1-(1-benzyl-2-isopropyl-5-(tetrahydropyran-2-yloxy)-1H-indol-3-yl)ethanol as a mixture of two diastereomers that were used directly in the next step without further purification or characterization. Thus, crude 1-(1-benzyl-2-isopropyl-5-(tetrahydropyran-2-yloxy)-1H-indol-3-yl)ethanol (200 mg, 0.51 mmol) was oxidized to 1-(1-benzyl-2-isopropyl-5-(tetrahydropyran-2-yloxy)-1H-indol-3-yl)ethanone (Compound 14) by General Procedure B.

$^1$H NMR (CDCl$_3$) δ 1.33 (d, J=7.3 Hz, 6H), 1.60-1.75 (br m, 4H), 1.95 (m, 1H), 2.02 (m, 1H), 2.72 (s, 3H), 3.60 (m, 1H), 4.00 (m, 1H), 4.10 (m, 1H), 5.41 (t, J=3.5 Hz, 1H), 5.46 (s, 2H), 6.93 (dd, J=7.5, 1.5 Hz, 1H), 6.97 (d, J=8.0 Hz, 2H), 7.03 (d, J=7.5 Hz, 1H), 7.26 (m, 3H), 7.61 (d, J=1.5 Hz, 1H).

Example 15

(E)-1-(1-Benzyl-5-hydroxy-2-isopropyl-1H-indol-3-yl)-3-phenylpropenone (Compound 15). To 1-(1-benzyl-2-isopropyl-5-(tetrahydropyran-2-yloxy)-1H-indol-3-yl)ethanone (125 mg, 0.32 mmol), was added benzaldehyde (PhCHO 37 mg, 0.35 mmol), EtOH (3 mL), and aqueous KOH (2 M solution, 0.5 mL), and the solution was stirred at ambient temperature for 48 h. The reaction was cooled to 0° C. and 10% aqueous HCl (2 mL) was added. The solution was diluted with EtOAc (30 mL), and washed with water, and 10% aqueous NaHCO$_3$, and brine (5 mL each), and dried (Na$_2$SO$_4$), and the solvent was removed under vacuum. The residue was purified by silica gel chromatography with 25% EtOAc in hexane to give (E)-1-(1-benzyl-5-hydroxy-2-isopropyl-1H-indol-3-yl)-3-phenylpropenone (Compound 15) as a pale yellow solid.

$^1$H NMR (CDCl$_3$) δ 1.38 (d, J=7.5 Hz, 6H), 3.84 (m, 1H), 5.46 (s, 2H), 6.74 (dd, J=7.5, 2.0 Hz, 1H), 6.96 (d, J=8.5 Hz, 2H), 6.98 (d, J=16 Hz, 1H), 7.27 (m, 3H), 7.33 (m, 4H), 7.45 (d, J=16 Hz, 1H), 7.60 (dd, J=7.5, 2.0 Hz, 2H), 7.71 (d, J=16 Hz, 1H).

Example 16

1-(1-Benzyl-5-hydroxy-2-isopropyl-1H-indol-3-yl)-3-phenylpropan-1-one (Compound 16). To a −78° C. solution of (E)-1-(1-benzyl-5-hydroxy-2-isopropyl-1H-indol-3-yl)-3-phenylpropenone (Compound 15, 60 mg, 0.15 mmol) was added a 1 M solution of LiAH$_4$ in THF (1 mL, 1 mmol). The solution was gradually warmed to 0° C. and then the reaction was quenched by adding EtOAc and water (1 mL each). The solution was diluted with EtOAc (30 mL), and the organic layer was washed with 10% aqueous HCl, and brine, and dried (Na$_2$SO$_4$), and the solvent was removed under vacuum. The residue was purified by preparative thin layer chromatography (TLC) using 30% EtOAc in hexane to produce 1-(1-benzyl-5-hydroxy-2-isopropyl-1H-indol-3-yl)-3-phenylpropan-1-one (Compound 16) as a colorless oil.

$^1$H NMR (CDCl$_3$) δ 1.34 (d, J=7.5 Hz, 6H), 3.14 (t, J=8.0 Hz, 2H), 3.33 (t, J=8.0 Hz, 2H), 4.05 (m, 1H), 5.46 (s, 2H), 6.74 (dd, J=7.5, 2.0 Hz, 1H), 6.96 (d, J=8.5 Hz, 2H), 6.98 (d, J=7.5 Hz, 1H), 7.30 (m, 9H).

Example 17

1-(1-Benzyl-5-hydroxy-2-isopropyl-1H-indol-3-yl)ethanone (Compound 17). General Procedure D. To a solution of 1-(1-benzyl-2-isopropyl-5-(tetrahydropyran-2-yloxy)-1H-indol-3-yl)ethanone (Compound 14, 60 mg, 0.16 mmol) in MeOH was added aq. HCl (1 mL), and the solution was stirred for 5 min. at room temperature. The reaction was quenched by adding 5% aqueous NaHCO$_3$ (2 mL), and the product was extracted with EtOAc (30 mL). The organic layer was separated, and washed with water, and brine, and dried (Na$_2$SO$_4$), and the solvent was removed under vacuum. Flash chromatography on silica gel with 20% EtOAc in hexane gave 1-(1-benzyl-5-hydroxy-2-isopropyl-1H-indol-3-yl)ethanone (Compound 17) as a white solid.

$^1$H NMR (CDCl$_3$) δ 1.35 (d, J=7.5 Hz, 6H), 2.69 (s, 3H), 4.02 (m, 1H), 5.46 (s, 2H), 6.76 (dd, J=7.5, 1.5 Hz, 1H), 6.94 (d, J=8.0 Hz, 2H), 6.98 (d, J=7.5 Hz, 1H), 7.26 (m, 3H), 7.49 (d, J=1.5 Hz, 1H).

Example 18

1-(1-Benzyl-2-isopropyl-5-(tetrahydrpyran-2-yloxy)-1H-indol-3-yl)butan-1-one (Compound 18). The title compound was prepared from 1-benzyl-2-isopropyl-5-(tetrahydropyran-2-yloxy)-1H-indole-3-carboxaldehyde (Compound 13) by General Procedure C.

$^1$H NMR (CDCl$_3$) δ 1.06 (t, J=7.0 Hz, 3H), 1.34 (d, J=7.5 Hz, 6H), 1.60-1.75 (br, m, 3H), 1.85 (m, 2H), 1.90 (m, 2H), 2.00-2.10 (br m, 1H), 3.02 (t, J=7.5 Hz, 2H), 2.97 (m, 1H), 4.00 (m, 2H), 5.39 (t, J=4.0 Hz, 1H), 5.45 (s, 2H), 6.93 (dd, J=9.0, 2.0 Hz, 1H), 6.94 (d, J=7.5 Hz, 2H), 7.03 (d, J=9.0 Hz, 1H), 7.25 (m, 3H), 7.59 (d, J=2.0 Hz, 1H).

Example 19

1-(1-Benzyl-5-hydroxy-2-isopropyl-1H-indol-3-yl)butan-1-one (Compound 19). The title compound was prepared from 1-(1-benzyl-2-isopropyl-5-(tetrahydrpyran-2-yloxy)-1H-indol-3-yl)butan-1-one (Compound 18) by General Procedure D.

$^1$H NMR (CDCl$_3$) δ 1.02 (t, J=7.5 Hz, 3H), 1.33 (d, J=7.5 Hz, 6H), 1.82 (m, 2H), 2.98 (t, J=7.5 Hz, 2H), 4.01 (br m, 1H), 5.45 (s, 2H), 6.73 (dd, J=8.0, 2.0 Hz, 1H), 6.94 (d, J=7.0 Hz, 2H), 6.98 (d, J=8.5 Hz, 1H), 7.26 (m, 3H), 7.39 (d, J=2.0 Hz, 1H).

Example 20

1-(1-Benzyl-2-isopropyl-5-(tetrahydrpyran-2-yloxy)-1H-indol-3-yl)-3-methylbutan-1-one (Compound 20). The title compound was prepared from 1-benzyl-2-isopropyl-5-(tetrahydropyran-2-yloxy)-1H-indole-3-carboxaldehyde (Compound 13) by General Procedure C.

$^1$H NMR (Acetone-d$_6$) δ 1.06 (d, J=7.5 Hz, 6H), 1.37 (d, J=7.5 Hz, 6H), 1.60-1.74 (br m, 3H), 1.90 (m, 2H), 2.39 (m, 1H), 2.92 (m, 2H), 3.62 (m, 1H), 3.95 (m, 1H), 3.99 (m, 1H), 5.44 (t, J=3.5 Hz, 1H), 5.64 (s, 2H), 6.94 (dd, J=9.0, 2.5 Hz, 1H), 7.04 (d, J=8.5 Hz, 2H), 7.32 (m, 4H), 7.66 (d, J=2.5 Hz, 1H).

Example 21

1-(1-Benzyl-5-hydroxy-2-isopropyl-1H-indol-3-yl)-3-methylbutan-1-one (Compound 21). The title compound was prepared from 1-(1-benzyl-2-isopropyl-5-(tetrahydrpyran-2-yloxy)-1H-indol-3-yl)-3-methylbutan-1-one (Compound 20) by General Procedure D.

$^1$H NMR (CDCl$_3$) δ 0.94 (d, J=7 Hz, 6H), 1.27 (d, J=7 Hz, 6H), 2.50 (m, 1H), 2.81 (d, J=7 Hz, 2H), 3.95 (m, 1H), 5.37 (s, 2H), 6.65 (dd, J=8.0, 2.0 Hz, 1H), 6.87 (d, J=7.5 Hz, 2H), 6.89 (d, J=8.5 Hz, 1H), 7.19 (m, 3H), 7.30 (d, J=2.0 Hz, 1H).

Example 22

1-(1-Benzyl-2-isopropyl-5-(tetrahydrpyran-2-yloxy)-1H-indol-3-yl)-2-phenylethan-1-one (Compound 22). The title compound was prepared from 1-benzyl-2-isopropyl-5-(tetrahydropyran-2-yloxy)-1H-indole-3-carboxaldehyde (Compound 13) by General Procedure C.

$^1$H NMR (CDCl$_3$) δ 1.28 (d, J=7.5 Hz, 6H), 1.60-1.73 (br m, 3H), 1.88 (m, 2H), 2.01 (m, 1H), 3.60 (m, 1H), 3.95-4.05 (br m, 2H), 4.39 (s, 2H), 5.39 (t, J=3.0 Hz, 1H), 5.46 (s, 2H), 6.94 (m, 3H), 7.05 (d, J=8.5 Hz, 1H), 7.20-7.38 (m, 8H), 7.68 (d, J=2.0 Hz, 1H).

Example 23

1-(1-Benzyl-5-hydroxy-2-isopropyl-1H-indol-3-yl)-2-phenylethan-1-one (Compound 23). The title compound was prepared from 1-(1-benzyl-2-isopropyl-5-(tetrahydrpyran-2-yloxy)-1H-indol-3-yl)-2-phenylethan-1-one (Compound 22) by General Procedure D.

$^1$H NMR (CDCl$_3$) δ 1.31 (d, J=7.5 Hz, 6H), 4.05 (m, 1H), 4.38 (S, 2H), 5.49 (s 2H), 6.74 (dd, J=8.5, 2.5 Hz, 1H), 6.97 (d, J=7.0 Hz, 2H), 7.02 (d, J=8.0 Hz, 1H), 7.32 (m, 8H), 7.46 (d, J=2.5 Hz, 1H).

Example 24

(1-Benzyl-5-hydroxy-2-isopropyl-1H-indol-3-yl)phenylmethanone (Compound 24). The title compound was prepared from 1-benzyl-2-isopropyl-5-(tetrahydropyran-2-yloxy)-1H-indole-3-carboxaldehyde (Compound 13) by General Procedure C and General Procedure D.

$^1$H NMR (CDCl$_3$) δ 1.35 (d, J=7.3 Hz, 6H), 3.50 (m, 1H), 5.41 (s, 2H), 6.41 (d, J=2.4 Hz, 1H), 6.67 (dd, J=8.3, 2.4 Hz, 1H), 7.00 (br s, 1H), 7.01 (d, J=8.0 Hz, 2H), 7.33 (m, 4H), 7.48 (t, J=7.5 Hz, 2H), 7.84 (d, J=8.0 Hz, 2H).

Example 25

(1-Benzyl-5-hydroxy-2-isopropyl-1H-indol-3-yl)-(4-butylphenyl)methanone (Compound 25). The title compound was prepared from 1-benzyl-2-isopropyl-5-(tetrahydropyran-2-yloxy)-1H-indole-3-carboxaldehyde (Compound 13) by General Procedure C and General Procedure D.

$^1$H NMR (CDCl$_3$) δ 1.01 (t, J=7.5 Hz, 3H), 1.35 (d, J=8.0 Hz, 6H), 1.36 (m, 2H), 1.72 (m, 2H), 2.70 (t, J=7.5 Hz, 2H), 3.58 (m, 1H), 5.57 (s, 2H), 6.57 (d, J=2.0 Hz, 1H), 6.69 (dd, J=8.0, 2.0 Hz, 1H), 7.02 (m, 3H), 7.30 (m, 5H), 7.79 (d, J=7.5 Hz, 2H).

SCHEME 7

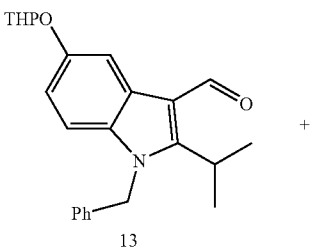

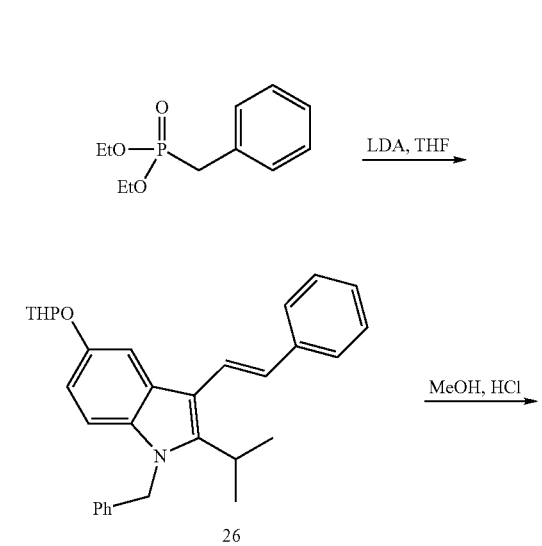

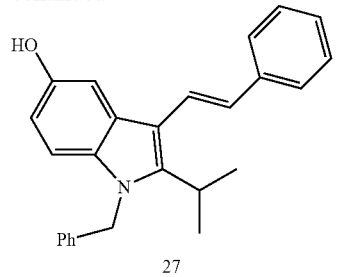

27

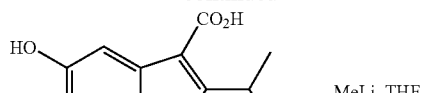

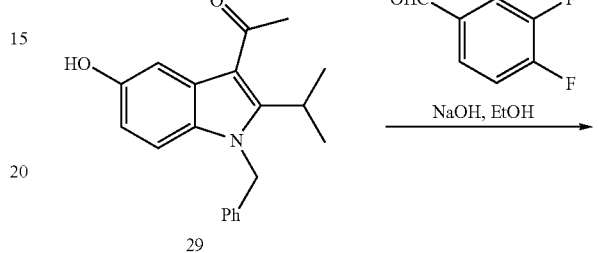

29

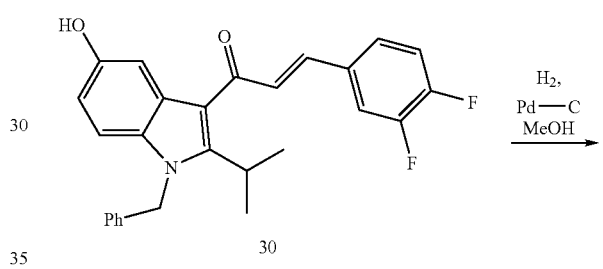

30

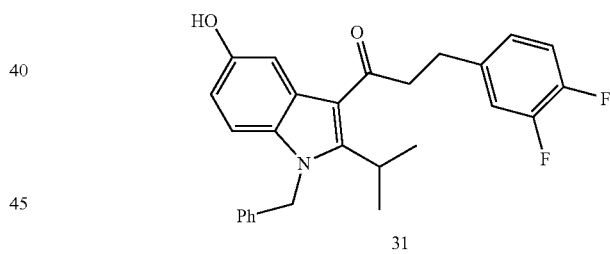

31

Example 26

(E)-1-Benzyl-2-isopropyl-3-(2-phenylethen-1-yl)-5-(tetrahydropyran-2-yloxy)-1H-indole (Compound 26). To a −78° C. solution of diethyl benzylphoshonate (91 mg, 0.4 mmol) in THF (5 mL) was added a 2 M solution of LDA and THF (0.2 mL, 0.4 mmol), and the solution was warmed to RT over 20 min. A solution of 1-benzyl-2-isopropyl-5-(tetrahydropyran-2-yloxy)-1H-indole-3-carboxaldehyde (Compound 13, 100 mg, 0.27 mmol) and THF (2 mL) was added, and the solution was stirred for 1 h at ambient temperature. The solution was diluted with EtOAc (50 mL), and washed with brine (10 mL), and dried ($Na_2SO_4$), and the solvent was removed under vacuum. Silica gel flash chromatography using 20% EtOAc in hexane gave (E)-1-benzyl-2-isopropyl-3-(2-phenylethen-1-yl)-5-(tetrahydropyran-2-yloxy)-1H-indole (Compound 26) as a colorless oil.

$^1$H NMR ($CDCl_3$) δ 1.41 (d, J=7.5 Hz, 6H), 1.60-1.75 (br m, 3H), 1.95 (m, 2H), 2.10 (m, 1H), 3.38 (m, 1H), 3.70 (m, 1H), 4.11 (m, 1H), 5.42 (s, 2H), 5.45 (t, J=3.0 Hz, 1H), 6.99 (m, 1H), 7.01 (d, J=8.0 Hz, 2H), 7.11 (dd, J=7.0, 3.0 Hz, 2H), 7.28 (m, 4H), 7.40 (t, J=7.5 Hz, 2H), 7.52 (dd, J=16.3, 2.0 Hz, 1H), 7.57 (d, J=8.0 Hz, 2H), 7.55 (t, J=2.0 Hz, 1H).

Example 27

(E)-1-Benzyl-5-hydroxy-2-isopropyl-3-(2-phenylethen-1-yl)-1H-indole (Compound 27). The title compound was prepared from (E)-1-benzyl-2-isopropyl-3-(2-phenylethen-1-yl)-5-(tetrahydropyran-2-yloxy)-1H-indole (Compound 26) by General Procedure D.

$^1$H NMR ($CDCl_3$) δ 1.42 (d, J=7.0 Hz, 6H), 3.37 (m, 1H), 5.41 (s, 2H), 6.76 (dd, J=8.0, 2.5 Hz, 1H), 7.01 (d, J=7.5 Hz, 2H), 7.06 (s, 1H), 7.09 (d, J=8.0 Hz, 1h), 7.29 (m, 5H), 7.40 (t, J=8.0, 2H), 7.51 (d, J=2.5 Hz, 1H), 7.53 (d, J=16.0 Hz, 1H), 7.56 (d, J=8.0 Hz, 2H).

SCHEME 8

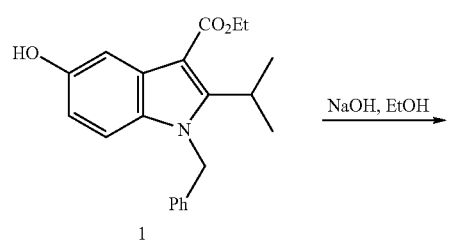

1

Example 28

1-Benzyl-5-hydroxy-2-isopropyl-1H-indole-3-carboxylic acid (Compound 28). General Procedure E. A solution of ethyl 1-benzyl-5-hydroxy-2-isopropyl-1H-indole-3-carboxylate (Compound 1, 1.1 g, 3.3 mmol) and NaOH (2.6 g, 65 mmol) in EtOH (20 ml) and $H_2O$ (10 ml) was heated to 100° C. for 16 h. The solvent was removed and the residue was treated with cold 6 M HCl (10.8 ml) and filtered. The resulting solid was washed with $H_2O$ (×3) and was taken in $Et_2O$ (∴3) to yield 1-benzyl-5-hydroxy-2-isopropyl-1H-indole-3-carboxylic acid (Compound 28) as a brown solid.

$^1$H NMR ($CD_3OD$) δ 1.35 (d, J=7.3 Hz, 6H), 3.88-4.02 (m, 1H), 5.52 (s, 2H), 6.67 (dd, J=8.8, 2.4 Hz, 1H), 6.95 (d, J=7.3 Hz, 2H), 7.05 (d, J=8.8 Hz, 1H), 7.19-7.30 (m, 3H), 7.58 (d, J=2.0 Hz, 1H).

Example 29

1-(1-Benzyl-5-hydroxy-2-isopropyl-1H-indol-3-yl)ethanone (Compound 29). General Procedure F. To a solution of 1-benzyl-5-hydroxy-2-isopropyl-1H-indole-3-carboxylic acid (Compound 28, 242 mg, 0.78 mmol) under argon was added methyllithium (3.0 M in diethoxymethane, 5.2 ml, 15.7 mmol) at room temperature. The reaction was stirred for 4 h and was quenched with 1 M HCl, extracted with EtOAc. The organic layer was washed with brine, dried over $Na_2SO_4$, and concentrated. The residue was purified by flash chromatography on silica gel eluting with 0-50% EtOAc-hexanes to yield 1-(1-benzyl-5-hydroxy-2-isopropyl-1H-indol-3-yl)ethanone (Compound 29) as a yellow solid.

$^1$H NMR (CDCl$_3$) δ 1.38 (d, J=7.3 Hz, 6H), 2.72 (s, 3H), 4.03-4.13 (m, 1H), 5.49 (s, 2H), 6.78 (dd, J=8.8, 2.4 Hz, 1H), 6.98 (d, J=6.8 Hz, 2H), 7.01 (d, J=8.8 Hz, 1H), 7.24-7.35 (m, 3H), 7.50 (d, J=2.4 Hz, 1H).

Example 30

(E)-1-(1-Benzyl-5-hydroxy-2-isopropyl-1H-indol-3-yl)-3-(3,4-difluorophenyl)prop-2-en-1-one (Compound 30). General Procedure G. To a solution of 1-(1-benzyl-5-hydroxy-2-isopropyl-1H-indol-3-yl)ethanone (Compound 29, 64 mg, 0.21 mmol) in EtOH (3 ml) and NaOH (4 M, 0.53 ml) at room temperature was added 3,4-difluorobenzaldehyde (46 µl, 0.42 mmol). The reaction was stirred for 16 h, heated to 60° C. for 4 h, and more 3,4-difluorobenzaldehyde (180 µl, 1.68 mmol) was added, stirred at room temperature for 24 h. The reaction was quenched by 1 M HCl (5 ml), and stirred at room temperature for 4 h, and the product was extracted with EtOAc. The layers were separated and the organic layer was washed with brine, and dried over $Na_2SO_4$, and concentrated under vacuum. The residue was purified by flash chromatography on silica gel eluting with 0-30% EtOAc-hexanes followed by PTLC (30% EtOAc-hexanes) to yield (E)-1-(1-benzyl-5-hydroxy-2-isopropyl-1H-indol-3-yl)-3-(3,4-difluorophenyl)prop-2-en-1-one (Compound 30) as a yellow solid.

$^1$H NMR (CDCl$_3$) δ 1.40 (d, J=6.8 Hz, 6H), 3.77-3.89 (m, 1H), 5.48 (s, 2H), 6.74 (dd, J=8.3, 2.4 Hz, 1H), 6.98 (d, J=7.3 Hz, 2H), 7.03 (d, J=8.8 Hz, 1H), 7.16-7.49 (m, 8H), 7.63 (d, J=16.1 Hz, 1H).

Example 31

1-(1-Benzyl-5-hydroxy-2-isopropyl-1H-indol-3-yl)-3-(3,4-difluorophenyl)propan-1-one (Compound 14). General Procedure H. To a solution of (E)-1-(1-benzyl-5-hydroxy-2-isopropyl-1H-indol-3-yl)-3-(3,4-difluorophenyl)prop-2-en-1-one (Compound 30, 25 mg, 0.058 mmol) in MeOH (2.0 ml) was added Pd—C (10%, 3.0 mg, 0.0029 mmol). The suspension was stirred under an atmosphere of hydrogen gas (1 atm) at room temperature for 2 h. The mixture was filtered through a pad of silica gel and concentrated. The residue was purified by PTLC (30% EtOAc-hexanes) to yield 1-(1-benzyl-5-hydroxy-2-isopropyl-1H-indol-3-yl)-3-(3,4-difluorophenyl)propan-1-one (Compound 31) as a light yellow solid.

$^1$H NMR (CDCl$_3$) δ 1.33 (d, J=7.3 Hz, 6H), 3.11 (t, J=7.3 Hz, 2H), 3.32 (t, J=7.6 Hz, 2H), 3.95-4.07 (m, 1H), 5.46 (s, 2H), 6.71 (dd, J=8.8, 2.0 Hz, 1H), 6.95 (d, J=6.8 Hz, 2H), 6.98-7.12 (m, 4H), 7.24-7.32 (m, 4H).

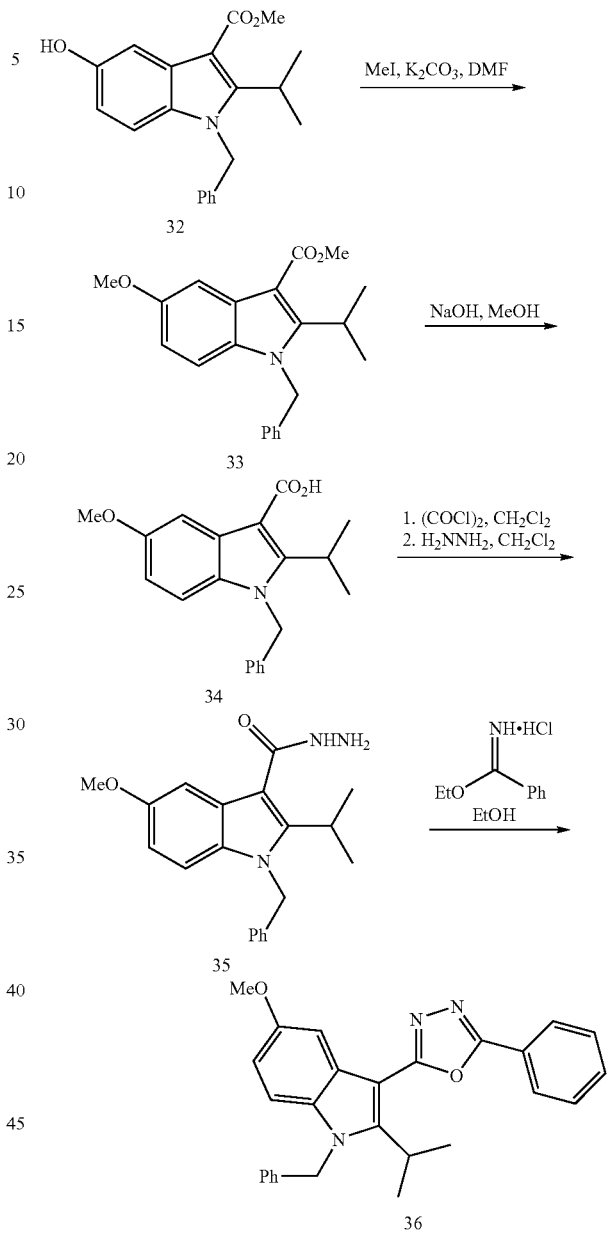

SCHEME 9

Example 32

Methyl 1-benzyl-5-hydroxy-2-isopropyl-1H-indole-3-carboxylate (Compound 32). The title compound was prepared from methyl isobutyrylacetate by General Procedure A.

1H NMR (CDCl$_3$) δ ppm 1.38 (d, J=6.8 Hz, 6H), 3.95 (s, 3H), 3.96-4.04 (m, 1 H), 5.46 (s, 2H), 6.73 (dd, J=8.5, 2.7 Hz, 1H), 6.95 (d, J=6.8 Hz, 2H), 7.00 (d, J=8.8 Hz, 1H), 7.23-7.32 (m, 3H), 7.61 (d, J=2.4 Hz, 1H).

Example 33

Methyl 1-benzyl-2-isopropyl-5-methoxy-1H-indole-3-carboxylate (Compound 33). To a solution of methyl 1-benzyl-5-hydroxy-2-isopropyl-1H-indole-3-carboxylate (Compound 32, 560 mg, 1.73 mmol) in DMF (6.0 ml) was added methyl iodide (0.32 ml, 5.20 mmol) and $K_2CO_3$ (718 mg, 5.20 mmol). The mixture was stirred at room temperature for 16 h, diluted with EtOAc, washed with $H_2O$, brine, dried over $Na_2SO_4$, and concentrated in vacuo. The residue was purified by flash chromatography on silica gel eluting with 0-20% EtOAc-hexanes to yield methyl 1-benzyl-2-isopropyl-5-methoxy-1H-indole-3-carboxylate (Compound 33) as a yellow solid.

1H NMR (CDCl$_3$) δ ppm 1.38 (d, J=6.8 Hz, 6H), 3.89 (s, 3H), 3.94-4.08 (m, 1 H), 3.96 (s, 3H), 5.47 (s, 2H), 6.81 (dd, J=9.0, 2.7 Hz, 1H), 6.95 (d, J=6.8 Hz, 2 H), 7.04 (d, J=8.8 Hz, 1H), 7.22-7.32 (m, 3H), 7.68 (d, J=2.4 Hz, 1H).

Example 34

1-Benzyl-2-isopropyl-5-methoxy-1H-indole-3-carboxylic acid (Compound 34). The title compound was prepared from methyl 1-benzyl-2-isopropyl-5-methoxy-1H-indole-3-carboxylate (Compound 33) by General Procedure E.

1H NMR (CDCl$_3$) δ ppm 1.42 (d, J=6.8 Hz, 6H), 3.92 (s, 3H), 4.04-4.20 (m, 1 H), 5.50 (s, 2H), 6.82 (dd, J=9.0, 2.7 Hz, 1H), 6.98 (d, J=6.8 Hz, 2H), 7.04 (d, J=8.8 Hz, 1H), 7.22-7.35 (m, 3H), 7.81 (d, J=2.4 Hz, 1H).

Example 35

1-Benzyl-2-isopropyl-5-methoxy-1H-indole-3-carbohydrazide (Compound 35). To a solution of 1-benzyl-2-isopropyl-5-methoxy-1H-indole-3-carboxylic acid (Compound 34, 260 mg, 0.81 mmol) in $CH_2Cl_2$ (5.0 ml) was added oxally chloride (2.0 M in $CH_2Cl_2$, 0.81 ml, 1.62 mmol) and 1 drop of DMF. The mixture was stirred at room temperature for 5 h and was concentrated in vacuo to yield 290 mg light brown solid. The crude product (205 mg, 0.6 mmol) was dissolved in $CH_2Cl_2$ (6.0 ml) and was treated with hydrazine (0.19 ml, 6.0 mmol) at room temperature for 5 h. The reaction was diluted with EtOAc, washed with $H_2O$, brine, dried over $Na_2SO_4$, and concentrated in vacuo. The residue was purified by flash chromatography on silica gel eluting with 30-100% EtOAc-hexanes and then 20% MeOH—$CH_2Cl_2$ to yield 1-benzyl-2-isopropyl-5-methoxy-1H-indole-3-carbohydrazide (Compound 35) as yellow syrup.

1H NMR (CDCl$_3$) δ ppm 1.37 (d, J=7.3 Hz, 6H), 3.65-3.75 (m, 1H), 3.84 (s, 3 H), 5.43 (s, 2H), 6.78 (dd, J=9.3, 2.4 Hz, 1H), 6.94 (d, J=6.8 Hz, 2H), 7.03 (d, J=8.8 Hz, 1H), 7.21-7.32 (m, 4H).

Example 36

2-(1-benzyl-2-isopropyl-5-methoxy-1H-indol-3-yl)-5-phenyl-1,3,4-oxadiazole (Compound 36). To a solution of 1-benzyl-2-isopropyl-5-methoxy-1H-indole-3-carbohydrazide (Compound 35, 25 mg, 0.074 mmol) in EtOH (2.0 ml) was added ethyl benzimidate hydrochloride (Fluka, 21 mg, 0.11 mmol). The mixture was stirred at 80° C. for 4 h and was concentrated in vacuo. The residue was purified by flash chromatography on silica gel eluting with 0-30% EtOAc-hexanes to yield 2-(1-benzyl-2-isopropyl-5-methoxy-1H-indol-3-yl)-5-phenyl-1,3,4-oxadiazole (Compound 36) as a white solid.

1H NMR (CDCl$_3$) δ ppm 1.48 (d, J=7.3 Hz, 6H), 3.92-4.04 (m, 1H), 3.95 (s, 3 H), 5.53 (s, 2H), 6.89 (dd, J=8.8, 2.4 Hz, 1H), 7.00 (d, J=6.8 Hz, 2H), 7.12 (d, J=9.3 Hz, 1H), 7.24-7.34 (m, 3H), 7.53-7.60 (m, 3H), 7.83 (d, J=2.4 Hz, 1H), 8.14-8.22 (m, J=6.8, 2.9 Hz, 2H).

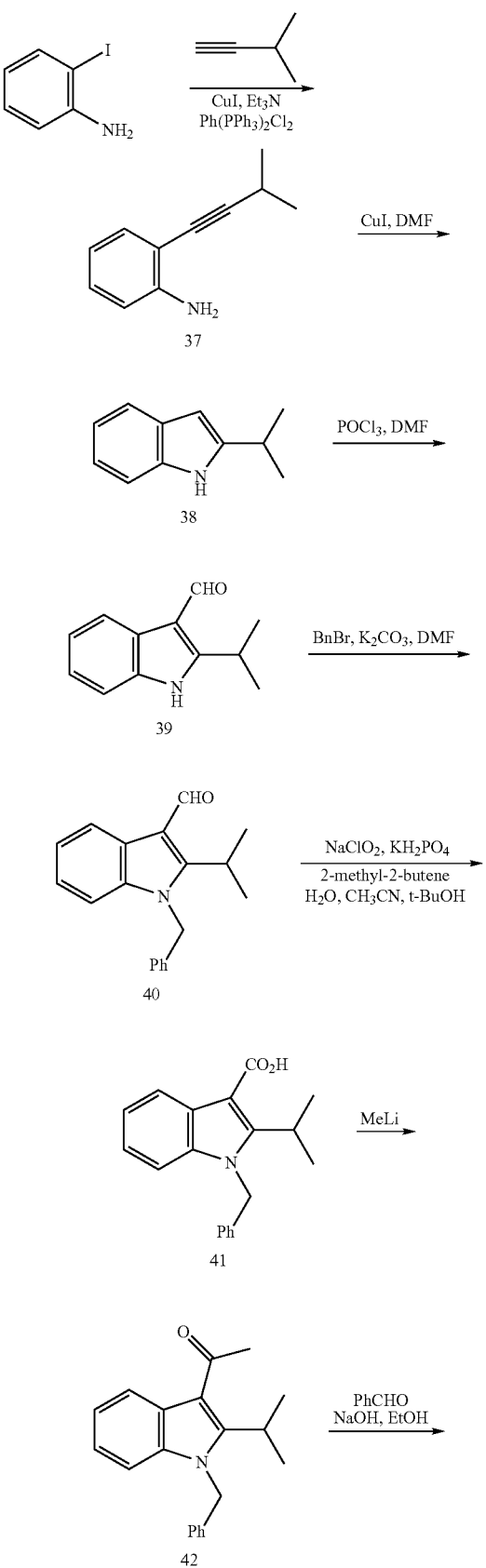

SCHEME 10

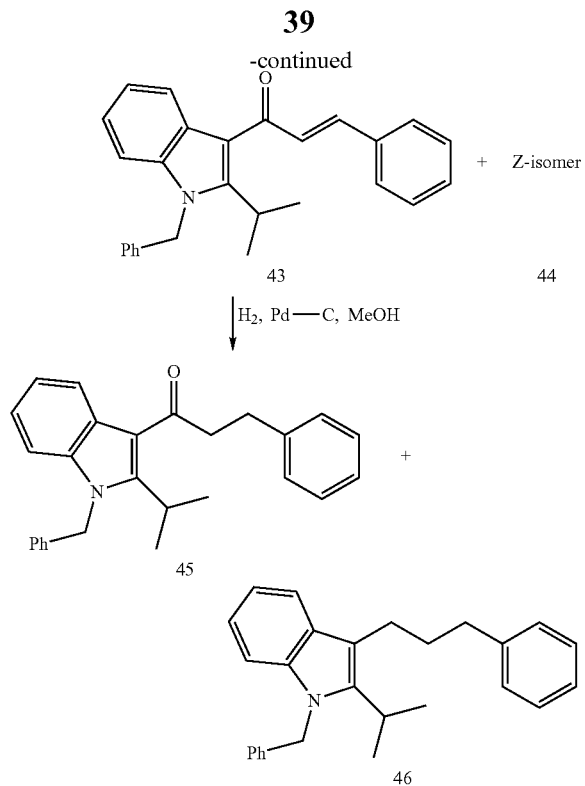

Example 37

2-(3-Methylbut-1-ynyl)aniline (Compound 37). To a solution of 2-iodoaniline (Aldrich, 5.0 g, 22.8 mmol) in Et₃N (50 ml) in a re-sealable pressure tube was added copper (I) iodide (22 mg, 0.114 mmol), Pd(PPh₃)₂Cl₂ (80 mg, 0.114 mmol), and 3-methylbut-1-yne (Alfa Aesar, 3.1 g, 45.7 mmol). The mixture was stirred at room temperature for 20 h and was diluted with Et₂O, filtered through Celite, and concentrated in vacuo. The residue was purified by flash chromatography on silica gel eluting with 30% Et₂O-hexanes to yield 2-(3-methylbut-1-ynyl)aniline (Compound 37) as orange oil.

1H NMR (CDCl₃) δ ppm 1.30 (d, J=6.8 Hz, 6H), 2.80-2.89 (m, 1H), 4.15 (s, 2 H), 6.64-6.71 (m, 2H), 7.05-7.10 (m, 1H), 7.24 (dd, J=7.8, 1.5 Hz, 1H).

Example 38

2-isopropyl-1H-indole (Compound 38). To a solution of 2-(3-methylbut-1-ynyl)aniline (Compound 37, 3.47 g, 21.8 mmol) in DMF (100 ml) was added copper (I) iodide (41 mg, 0.22 mmol). The mixture was stirred at 160° C. for 2 h and was concentrated in vacuo. The residue was purified by flash chromatography on silica gel eluting with 5% EtOAc-hexanes to yield 2-isopropyl-1H-indole (Compound 38) as an off-white solid.

1H NMR (CDCl₃) δ ppm 1.37 (d, J=6.8 Hz, 6H), 3.02-3.15 (m, 1H), 6.25 (s, 1 H), 7.07 (t, J=7.3 Hz, 1H), 7.12 (t, J=7.6 Hz, 1H), 7.32 (d, J=8.3 Hz, 1H), 7.54 (d, J=7.8 Hz, 1H), 7.91 (s, 1H).

Example 39

2-isopropyl-1H-indole-3-carbaldehyde (Compound 39). POCl₃ (0.86 ml, 9.4 mmol) was added dropwise to anhydrous DMF (4 ml) at 0° C. with stirring. After 30 min, this solution was added dropwise to a solution of 2-isopropyl-1H-indole (Compound 38, 1.24 g, 7.8 mmol) in DMF (16 ml) at 0° C. under argon. The reaction was stirred for 1 h while it warmed up to room temperature. The reaction was diluted with EtOAc, washed with aq. NaHCO₃, brine, dried over Na₂SO₄, and concentrated in vacuo. The residual solid was washed with Et₂O to yield 2-isopropyl-1H-indole-3-carbaldehyde (Compound 39) as a beige solid.

1H NMR (CDCl₃) δ ppm 1.48 (d, J=6.8 Hz, 6H), 3.76-3.88 (m, 1H), 7.23-7.32 (m, 2H), 7.37-7.42 (m, 1H), 8.23-8.30 (m, 1H), 8.75 (br s, 1H), 10.25 (s, 1H).

Example 40

1-Benzyl-2-isopropyl-1H-indole-3-carbaldehyde (Compound 40). To a solution of 2-isopropyl-1H-indole-3-carbaldehyde (Compound 39, 1.19 g, 6.4 mmol) in DMF (6.0 ml) was added benzyl bromide (1.5 ml, 12.8 mmol) and K₂CO₃ (2.65 g, 19.2 mmol). The mixture was stirred at room temperature for 24 h and was diluted with EtOAc, washed with H₂O, brine, dried over Na₂SO₄, and concentrated in vacuo. The residue was purified by flash chromatography on silica gel eluting with 0-30% EtOAc-hexanes to yield 1-benzyl-2-isopropyl-1H-indole-3-carbaldehyde (Compound 40) as a light brown solid.

1H NMR (CDCl₃) δ ppm 1.47 (d, J=7.3 Hz, 6H), 3.45-3.58 (m, 1H), 5.47 (s, 2 H), 7.00 (d, J=6.3 Hz, 2H), 7.22-7.34 (m, 6H), 8.40 (d, J=7.8 Hz, 1H), 10.47 (s, 1H).

Example 41

1-Benzyl-2-isopropyl-1H-indole-3-carboxylic acid (Compound 41). To a suspension of 1-benzyl-2-isopropyl-1H-indole-3-carbaldehyde (Compound 40, 545 mg, 2.0 mmol) in acetonitrile (6 ml), tert-butanol (6 ml) and H₂O (12 ml) was added 2-methyl-2-butene (8 ml), potassium phosphate monobasic (5.4 g, 40 mmol), sodium chlorite (80%, 2.3 g, 40 mmol). The mixture was stirred at room temperature for 16 h, more potassium phosphate monobasic (5.4 g, 40 mmol) and sodium chlorite (80%, 2.3 g, 40 mmol) were added and the mixture was stirred at room temperature for an additional 24 h, at which time more potassium phosphate monobasic (5.4 g, 40 mmol), sodium chlorite (80%, 2.3 g, 40 mmol), H₂O (8 ml), and 2-methyl-2-butene (8 ml) were added and the mixture was stirred for another 48 h. The solvent was removed in vacuo and the residual solid was washed with CHCl₃ (×3) and filtered. The filtrate was concentrated and was purified by flash chromatography on silica gel eluting with 0-20% EtOAc-hexanes to yield 1-benzyl-2-isopropyl-1H-indole-3-carboxylic acid (Compound 41) as a yellow solid.

1H NMR (CDCl₃) δ ppm 1.43 (d, J=7.3 Hz, 6H), 4.03-4.19 (m, 1H), 5.54 (s, 2 H), 6.99 (d, J=6.8 Hz, 2H), 7.16-7.21 (m, 2H), 7.23-7.34 (m, 4H), 8.32 (d, J=8.8 Hz, 1H).

Example 42

1-(1-Benzyl-2-isopropyl-1H-indol-3-yl)ethanone (Compound 42). The title compound was prepared from 1-benzyl-2-isopropyl-1H-indole-3-carboxylic acid (Compound 41) by General Procedure F.

1H NMR (CDCl₃) δ ppm 1.37 (d, J=7.3 Hz, 6H), 2.77 (s, 3H), 4.03-4.18 (m, 1 H), 5.53 (s, 2H), 6.97 (d, J=6.8 Hz, 2H), 7.18 (d, J=3.9 Hz, 2H), 7.23-7.33 (m, 4 H), 7.94 (d, J=8.3 Hz, 1H).

Example 43

(E)-1-(1-Benzyl-2-isopropyl-1H-indol-3-yl)-3-phenyl-prop-2-en-1-one (Compound 43). The title compound was prepared from 1-(1-benzyl-2-isopropyl-1H-indol-3-yl)ethanone (Compound 42) and benzaldehyde by General Procedure G.

1H NMR (CDCl₃) δ ppm 1.41 (d, J=7.3 Hz, 6H), 3.78-3.91 (m, 1H), 5.52 (s, 2 H), 6.99 (d, J=7.3 Hz, 2H), 7.13-7.32 (m, 6H), 7.38-7.45 (m, 3H), 7.53 (d, J=15.6 Hz, 1H), 7.63-7.67 (m, 2H), 7.74 (d, J=15.6 Hz, 1H), 7.83 (d, J=7.8 Hz, 1H).

Example 44

(Z)-1-(1-Benzyl-2-isopropyl-1H-indol-3-yl)-3-phenylprop-2-en-1-one (Compound 44). The title compound was isolated as a bi-product in the synthesis of Compound 43.

1H NMR (CDCl₃) δ ppm 1.37 (d, J=7.3 Hz, 6H), 4.04-4.16 (m, 1H), 5.50 (s, 2 H), 6.75 (d, J=12.7 Hz, 1H), 6.88 (d, J=6.8 Hz, 2H), 6.92 (d, J=12.7 Hz, 1 H), 7.07-7.10 (m, 1H), 7.13 (t, J=7.6 Hz, 1H), 7.17-7.22 (m, 4H), 7.24-7.31 (m, 3 H), 7.46-7.51 (m, 2H), 8.14 (d, J=7.8 Hz, 1H).

Example 45

1-(1-Benzyl-2-isopropyl-1H-indol-3-yl)-3-phenylpropan-1-one (Compound 45). The title compound was prepared from (E)-1-(1-benzyl-2-isopropyl-1H-indol-3-yl)-3-phenylprop-2-en-1-one (Compound 43) by General Procedure H.

1H NMR (CDCl₃) δ ppm 1.34 (d, J=7.3 Hz, 6H), 3.13-3.18 (m, 2H), 3.39-3.45 (m, 2H), 3.98-4.09 (m, 1H), 5.49 (s, 2H), 6.95 (d, J=6.8 Hz, 2H), 7.10-7.33 (m, 11H), 7.86 (d, J=7.8 Hz, 1H).

Example 46

1-Benzyl-2-isopropyl-3-(3-phenylpropyl)-1H-indole (Compound 46). The title compound was isolated as a bi-product in the synthesis of Compound 45.

1H NMR (CDCl₃) δ ppm 1.26 (d, J=7.3 Hz, 6H), 1.96-2.05 (m, 2H), 2.73-2.79 (m, 2H), 2.84-2.90 (m, 2H), 3.13-3.25 (m, 1H), 5.37 (s, 2H), 6.91 (d, J=6.8 Hz, 2H), 7.03-7.13 (m, 3H), 7.16-7.31 (m, 8H), 7.49 (dd, J=6.1, 3.2 Hz, 1 H).

The foregoing description details specific methods and compositions that can be employed to practice the present invention, and represents the best mode contemplated. Thus, however detailed the foregoing may appear in text, it should not be construed as limiting the overall scope hereof, rather, the ambit of the present invention was to be governed only by the lawful construction of the appended claims.

In particular, the present invention discloses and claims 3-substituted N-benzyl indoles wherein said 3-substitutent is represented by the formula $(R^4)_n Y-A^2-X-B-A^1$- wherein:

$R^4, Y, A^2, X, B$ and $A^1$ are as defined above. Preferably said 3-substituted N-benzyl indole is a 2-isopropyl substituted derivative.

What is claimed is:
1. A compound represented by the general formula

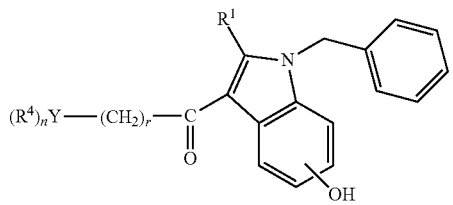

wherein n is 0 or an integer of from 1 to 6;
r is 0 or an integer of from 1 to 6;

Y is $R^6$, or a carbocyclic aryl group comprising from 6 to 14 carbon atoms $R^1$ is straight or branched chain alkyl having 2 to 12 carbons;

$R^4$ is selected from the group consisting of hydrogen, straight or branched chain alkyl having 1 to 12 carbons, cycloalkyl having 3 to 6 carbons, alkenyl having 2 to 6 carbons and 1 or 2 double bonds, alkynyl having 2 to 6 carbons and 1 or 2 triple bonds, aryl, halo, $C_1$ to $C_{12}$ haloalkyl, hydroxy, $C_1$ to $C_{12}$ alkoxy, $C_1$ to $C_{12}$ alkylcarbonyl, formyl, oxycarbonyl, carboxy, $C_1$ to $C_{12}$ alkyl carboxylate, $C_1$ to $C_{12}$ alkyl amide, aminocarbonyl, amino, cyano, diazo, nitro, thio, sulfoxyl, sulfonyl,

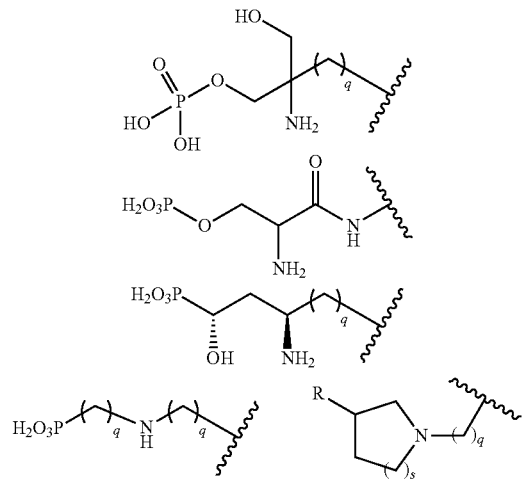

wherein R is $CO_2H$ or $PO_3H_2$ and q is 0 or an integer of 1 to 5 and s is 0 or an integer from 1 to 3; and $R^6$ is selected from the group consisting of straight or branched chain alkyl having 1 to 12 carbons, cycloalkyl having 3 to 6 carbons, alkenyl having 2 to 6 carbons and 1 or 2 double bonds and alkynyl having 2 to 6 carbons and 1 or 2 triple bonds.

2. The compound of claim 1 wherein said aryl group is selected from the group consisting of benzene, pyridine, pyrazine, pyridazine, pyrimidine, triazine, thiophene, furan, thiazole, thiadiazole, isothiazole, oxazole, oxadiazole, isooxazole, naphthalene, quinoline, tetralin, chroman, thiochroman, tetrahydroquinoline, dihydronaphthalene, tetrahydronaphthalene, chromene, thiochromene, dihydroquinoline, indan, dihydrobenzofuran, dihydrobenzothiophene, indene, benzofuran, benzothiophene, coumarin and coumarinone, which aryl is unsubstituted or is substituted with one or two alkyl, alkenyl, alkynyl, aryl, halo, haloalkyl, hydroxyl, alkoxyl, alkylcarbonyl, formyl, oxycarbonyl, carboxyl, alkyl carboxylate, alkyl amide, aminocarbonyl, amino, cyano, diazo, nitro, thio, sulfoxyl, or sulfonyl groups.

3. The compound of claim 1 wherein $R^1$ is i-propyl.

4. The compound of claim 1 wherein Y is selected from the group consisting of phenyl and 2,5 difluoro phenyl.

5. The compound of claim 1 wherein X is ethyl.

6. The compound of claim 1 selected from the group consisting of

1-Benzyl-3-((3,5-difluorobenzylamino)methyl)-2-isopropyl-1H-indol-5-ol, (E)-1-Benzyl-5-hydroxy-2-isopropyl-1H-indole-3-carboxaldehyde, O-Benzyl Oxime, (E)-1-Benzyl-5-hydroxy-2-isopropyl-1H-indole-3-carbaldehyde, O-Phenyl Oxime, (E)-1-(1-Benzyl-5-hydroxy-2-isopropyl-1H-indol-3-yl)-3-phenylpropenone,
1-(1-Benzyl-5-hydroxy-2-isopropyl-1H-indol-3-yl)-3-phenylpropan-1-one, 1-(1-Benzyl-5-hydroxy-2-isopropyl-1H-indol-3-yl)ethanone,
1-(1-Benzyl-5-hydroxy-2-isopropyl-1H-indol-3-yl)butan-1-one,
1-(1-Benzyl-5-hydroxy-2-isopropyl-1H-indol-3-yl)-3-methylbutan-1-one,
1-(1-Benzyl-5-hydroxy-2-isopropyl-1H-indol-3-yl)-2-phenylethan-1-one, (E)-1-(1-Benzyl-5-hydroxy-2-isopropyl-1H-indol-3-yl)-3-(3,4-difluorophenyl)prop-2-en-1-one, and
1-(1-Benzyl-5-hydroxy-2-isopropyl-1H-indol-3-yl)-3-(3,4-difluorophenyl)propan-1-one.

7. A composition comprising a compound represented by the formula selected from the group consisting of:

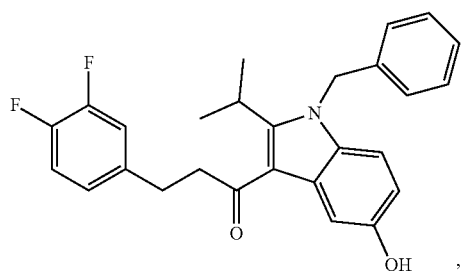

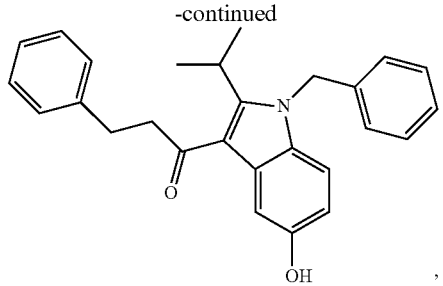

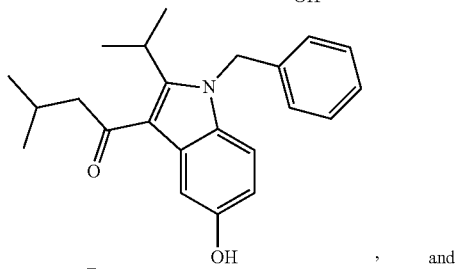

, and

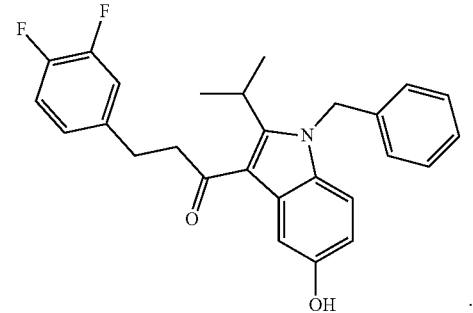

.

* * * * *